US006242196B1

(12) United States Patent
Spiegelman et al.

(10) Patent No.: US 6,242,196 B1
(45) Date of Patent: Jun. 5, 2001

(54) METHODS AND PHARMACEUTICAL COMPOSITIONS FOR INHIBITING TUMOR CELL GROWTH

(75) Inventors: Bruce M. Spiegelman, Waban; Soner Altiok, Cambridge; Elisabetta Mueller; Pasha Sarraf, both of Boston, all of MA (US); Peter Tontonoz, San Diego, CA (US)

(73) Assignee: Dana-Farber Cancer Institute, Boston, MA (US)

( * ) Notice: Subject to any disclaimer, the term of this patent is extended or adjusted under 35 U.S.C. 154(b) by 0 days.

(21) Appl. No.: 09/319,769

(22) PCT Filed: Dec. 11, 1997

(86) PCT No.: PCT/US97/22879

§ 371 Date: Sep. 17, 1999

§ 102(e) Date: Sep. 17, 1999

(87) PCT Pub. No.: WO98/25598

PCT Pub. Date: Jun. 18, 1998

(51) Int. Cl.[7] .............................. C12Q 1/34; C12Q 1/00; G01N 33/53
(52) U.S. Cl. ................... 435/7.1; 435/4; 435/18; 548/146
(58) Field of Search ................... 435/7.1, 4, 18; 548/146

(56) References Cited

U.S. PATENT DOCUMENTS

| 5,071,773 | 12/1991 | Evans et al. ............... 436/501 |
| 5,466,861 | 11/1995 | Dawson et al. ............ 560/100 |
| 5,514,821 | 5/1996 | Bennani et al. ............ 554/221 |
| 5,521,202 | 5/1996 | Yano et al. ............... 514/369 |
| 5,552,271 | 9/1996 | Pfahl et al. ............... 435/6 |

FOREIGN PATENT DOCUMENTS

| 93/21146 | 10/1993 | (WO) . |
| 95/10271 | 4/1995 | (WO) . |
| 95/11974 | 5/1995 | (WO) . |
| 95/18533 | 7/1995 | (WO) . |
| 95/35108 | 12/1995 | (WO) . |

(List continued on next page.)

OTHER PUBLICATIONS

Shao et al., Nature (London), vol. 396 (6709), pp. 377–380 (Abstract Only), 1998. Month Not Available.*
Adachi, H. et al., "Suppression by retinoids of the suppression by retioids of the induction of the CCAAT/enhancer–binding protein alpha and the nuclear receptors ppargamma and rogamma during adipocyte differentiation of 3t3–I1 cells," *Mol. Cell. Defferentitation*, 4:365–381 (1996). Month not available.

(List continued on next page.)

*Primary Examiner*—Louise N. Leary
(74) *Attorney, Agent, or Firm*—Lahive & Cockfield, LLP; Amy E. Mandragouras; DeAnn F. Smith

(57) ABSTRACT

A method for inhibiting proliferation of a PPAR γ-responsive hyperproliferative cell which comprises the step of contacting the cell with (I) an inhibitory amount of a PPARγ agonist and (II) a MAP kinase inhibitor is disclosed. A method for treating or prophylactically preventing in an animal subject a disorder characterized by unwanted proliferation of PPARγ-responsive hyperproliferative cells which comprises administering to the subject (I) an inhibitory amount of a PPARγ agonist and (II) a MAP kinase inhibitor is also disclosed. Pharmaceutical compositions comprising a therapeutically effective amount of a PPARγ agonist and a MAP kinase inhibitor are disclosed for use in the methods.

35 Claims, 24 Drawing Sheets

FOREIGN PATENT DOCUMENTS

| | | |
|---|---|---|
| 96/01317 | 1/1996 | (WO) . |
| 96/01430 | 1/1996 | (WO) . |
| 96/05165 | 2/1996 | (WO) . |
| 96/33724 | 10/1996 | (WO) . |
| 96/34943 | 11/1996 | (WO) . |
| 96/40128 | 12/1996 | (WO) . |
| 9717091 | 5/1997 | (WO) . |

OTHER PUBLICATIONS

Allen, P.W. "Recent Advances in Tumors of Adipose Tissue, "(1995) *Current Topics in Pathology* 89:215–239. Month not available.

Asou et al., "Growth Inhibition of Myeloid Leukemia Cells by Troglitazone, a Ligand for Peroxysome Proliferator Activated receptor gamma (PPAR gamma) and Retinoids, "(1997) *Blood* 90:284B. Month not available.

Bocos, C. et al., "Fatty Acid Activation of Peroxisome Proliferator–activated Receptor (PPAR)," (1995) *J. Steroid Biochem. Molec. Biol.* 53:467–473. Month not available.

Braissant, O. et al., "Differential Expression of Peroxisome Proliferator–Activated Receptors (PPARs): Tissue Distribution of PPAR–α, β, and γ in the Adult Rat," (1996) *Endocrinology* 137:354–366. Month not available.

Espandiari, P. et al., "The Herbicide Dicamba (2–Methoxy–3,6–dichlorobenzoic Acid) Is a Peroxisome Proliferator in Rats," (1995) *Fundamental and Applied Toxicology* 26:85–90. Month not available.

Ez–Zoubir, A. et al., "Cloning of a Protein That Mediates Transcriptional Effects of Fatty Acids in Preadipocytes," (1995) *The Journal of Biological Chemistry* 270:2367–2371. Month not available.

Fleisch, J. et al., "A Brief Review of Preclinical and Clinical Studies with LY171883 and Some Comments on Newer Cysteinyl Leukotriene Receptor Antagonists," *Annals New York Academy of Sciences* pp. 356–368. Month not available.

Forman, B. et al., "15–Deoxy–Δ–Prostaglandin $J_2$ Is a Ligand for the Adipocyte Determination Factor PARγ," (1995) *Cell* 83:803–812. Month not available.

Green, S. et al. "Peroxisome proliferator–activated receptors: finding the orphan a home," (1994) *Molecular and Cellular Endocrinology* 100:149–153. Month not available.

Green, S. "PPAR: a mediator of peroxisome proliferator action," (1995) *Mutation Research* 333:101–109. Month not available.

Green, S. et al., "The molecular mechanism of peroxisome proliferator action: a model for species differences and mechanistic risk assessment," (1992) *Toxicology Letters* 64/65:131–139. Month not available.

Hertz, R. et al., "Mode of Action of Peroxisome Proliferators as Hypolipidemic Durgs," (1995) *The Journal of Biological Chemistry* 270–13475. Month not available.

Juge–Aubry, C. et al., "Peroxisome Proliferator–activated Receptor Mediates Cross–talk with Thyroid Hormone Receptor by Competition for Retinoid X Receptor," (1995) *The Journal of Biological Chemistry* 270:18117–18122. Month not available.

Kiyoto Motojima: "Peroxisome Proliferator–Activated Receptor (PPAR): Structure, Mechanisms of Activation and Diverse Functions," (1993) *Cell Structure and Function* 18:267–277. Month not available.

Kliewer, S. et al., "A Prostaglandin $J_2$ Metabolite Binds Peroxisome Proliferator–Activated Receptor γ and Promotes Adipocyte Differentiation," (1995) *Cell* 83:813–819. Month not available.

Lambe et al. "A human peroxysome–proliferator–activated receptor gamma is activated y inducers of adipogenesis, including thiazolidinedione drugs," *Eur. J. Biochem.*, 239:1–7 (1996). Month not available.

Lefébvre, P. et al., "Improving the action of insulin," (1995) *Clin. Invest. Med.* 18:340–347. Month not available.

Lehmann, J. et al., "An Antidiabetic Thiazolidinedione Is a High Affinity Ligand for Peroxisome Proliferator–activated Receptor γ (PPARγ)," (1995) *The Journal of Biological Chemistry* 270L12953–12956. Month not available.

Lehmann, et al., Retinoids Selective for Retinoid X Receptro Response Pathways, (1996) *Science,* 258:1944–1946. Month not available.

Motojima, K., "Peroxisome Proliferator–Activated Receptor (PPAR): Structure, Mechanisms of Activaton and Diverse Functions," (1993) *Cell Structure and Function* 18:267–277. Month not available.

Niemic, S. et al., "Influence of Nonionic Liposomal Composition on Topical Delivery of Peptide Drugs into Pilosebaceous Units: An in Vivo Study Using the Hamster Ear Model," (1995) *Pharmaceutical Research* 12:1184–1188. Month not available.

Nilsson, A. et al., "Potentiating effects of clofibric acid on the differentiation of HL–60 human promyelocytic leukemia cells induced by retinoids," (1995) *European Journal of Cell Biology* 67:379–385. Month not available.

Palmer, C. et al., "Novel Sequence Determinants in Peroxisome Proliferator Signaling," (1995) *The Journal of Biological Chemistry* 270:16114–16121. Month not available.

Schoonjans, K. et al., "The peroxisome proliferator activated receptors (PPARs) and their effects on lipid metabolism and adipocyte differentiation," (1996) *Biochimica et Biophysi Acta* 1302:93–109. Month not available.

Shao et al: "Peroxisome Proliferator Activated Receptor Gamma, CCAA/Enhancer–Binding Protein Alpha, and Cell Cycle Status Regulate the Commiment to Adipocyte Differentiation," (1997) *J. Biol. Chem.* 272:21473–21478. Month not available.

Smith, W., "The eicosanoids and their biochemical mechanisms of action," (1989) *Biochem. J.* 259:315–324. Month not available.

Smith, W., "Prostanoid biosynthesis and mechanisms of action," (1992) pp. F181–F191. Month not available.

Spiegelman et al., "PPAR–gamma and the Transcriptional Basis of Adipogenesis," (1997) *FASEB Journal* 11:a880. Month not available.

Sreekantaiah, C. et al., "Chromosomal Aberrations in Soft Tissue Tumors: Relevance to Diagnosis, Classification, and Molecular Mechanisms," (1994) *American Journal of Pathology* 144:1121–1134. Month not available.

Stunnenberg, H., "Mechanisms of Transactivation by Retinoic Acid Receptors," (1993) *BioEssays* 15:309–315. Month not available.

Tontonoz, P. et al., "Terminal differentiation of human liposarcoma cells induced by ligands for peroxisome proliferator–activated receptor gamma and the retinoid X receptor," *Proc Natl Acad Sci U S A.,* 94(1):237–41 (1997). Month not available.

Vaickus, L. et al., "Immune markers in hematologic malignancies," (1991) *Critical Reviews in Oncology/Hematology* 11:267–297. Month not available.

Varanasi, U. et al., "Identification of a Peroxisome Proliferator–responsive Element Upstream of the Human Peroxisomal Fatty Acyl Coenzyme A Oxidase Gene," (1996) *The Journal of Biological Chemistry* 271:2147–2155. Month not available.

Weinstock et al., "Pioglitazone: in vitro effects on rat hepatoma cells and in vivo liver hypertrophy in KKAy mice," *Pharmacology.*, 54(4):169–78 (1997). Month not available.

Yu, K. et al. "Differential activation of peroxisome proliferator–activated receptors by eicosanoids," *J. Biol. Chem.*, 270:23975–23983 (1995). Month not available

* cited by examiner

KEY:
FAT—normal human adipose tissue
ZR, BT, SK, MCF7— breast cancer cell lines
21-PT, 21-Nt, 21-PT—breast cancer cell line series
U937, HL60—hematopoietic cancer cell lines
RT112—Transitional cell bladder carcinoma
JMN1B—Mesothelioma
DU145, PC-3—Prostatic cancer cell lines
1650—Kidney SV-40 transformed
1609— Skin transformed
1420—Pancreatic cancer
CX-1, MRC-5—colon carcinoma Control Troglitazone Pioglitazone Control Troglitazone 15deoxy $\Delta^{12,14}$ PGJ2

M2

Control

Troglitazone

Pioglitazone

CONTROL

TROGLITAZONE

PD 98059

TROGLITAZONE + PD 98059

METHODS AND PHARMACEUTICAL COMPOSITIONS FOR INHIBITING TUMOR CELL GROWTH

BACKGROUND OF THE INVENTION

Adipocytes are highly specialized cells that play a critical role in energy and homeostasis. Their primary role is to store triglycerides in times of caloric excess and to mobilize this reserve during periods of nutritional deprivation. Adipocytes are derived from a multipotent stem cell of mesodermal origin that also gives rise to the muscle and cartilage lineages. Adipocyte differentiation is characterized by a coordinate increase in adipocyte-specific gene expression.

Recent years have seen important advances in our understanding of the molecular basis of adipocyte differentiation. (reviewed in Cornelius, P. et al. (1994) *Annu. Rev. Nutr.* 14:99–129; Tontonoz, P. et al. (1995) *Curr. Opin. Genet. Dev.* 5:571–576. A number of transcription factors are induced in fat cell differentiation (C/EBPα, C/EBPβ and ADD1/SREBP1) and influence this process to a certain extent (Freytag, S. O. et al. (1994) *Genes Dev.* 8:1654–63; Kim, J. B. and Spiegelman, B. M. (1996) *Genes Dev.* 10:1096–1107; Lin, F. T. and Laane, M. D. (1994) *PNAS USA* 91:8757–61; Samuelsson, L. et al. (1991) *EMBO J.* 10:3787–93; Tontonoz, P. et al. (1993) *Mol Cell Biol* 13:4753–9; Umek, R. M. et al. (1991) *Science* 251:288–92; Wu, C. L. et al. (1995) *Mol Cell Biol* 15:253646; Yeh, W. C. et al. (1995) *Genes Dev.* 9:168–81).

The peroxisome proliferator-activated receptors, or "PPAR", are members of the type II class of steroid/thyroid superfamily of receptors and mediate the pleiotropic effects of peroxisome proliferators. Type II class of nuclear receptors includes PPAR, the thyroid hormone receptor ($T_3R$), and the vitamin $D_3$ receptor ($VD_3R$). Type II receptors are functionally distinct from the classical steroid receptors, such as the glucocorticoid receptor, the progesterone receptor and the estrogen receptor (reviewed in Stunnenberg, H. G. (1993) *BioEssays Vol.* 15 (5): 309–15). Three properties distinguish these two classes. First, type II receptors are able to bind to their responsive elements in the absence of ligand (Damm et al. (1989) *Nature* 339:593–597; Sap et al., *Nature* 340:242–244; De The et al. (1990) *Nature* 343:177–180), whereas ligand binding is required to dissociate to the type I receptor-hsp 90 complex and hence indirectly governs DNA binding. Second, type II receptors bind and transactivate through responsive elements that are composed of half-sites arranged as direct repeats, as opposed to palindromically arranged half-sites invariably separated by three nucleotides required by type I receptors. Finally, type II receptors do not bind to their respective binding sites as homodimers but require an auxiliary factor, RXR (e.g., RXRα, RXRβ, RXRγ) for high affinity binding (Yu et al. (1991) *Cell* 67:1251–1266; Bugge et al. (1992) *EMBO J.* 11:1409–1418; Kliewer et al. (1992) *Nature* 355:446–449; Leid et al. (1992) *Cell* 68:377–395; Marks et al. (1992) *EMBO J.* 11:1419–1435; Zhang et al. (1992) *Nature* 355:441–446). The interaction between type II receptors requires a region in the C-terminal domain (Yu et al. (1991) *Cell* 67:1251–1266; Kliewer et al. (1992) *Nature* 355:446–449; Leid et al. (1992) *Cell* 68:377–395; Marks et al. (1992) *EMBO J.* 11:1419–1435). Following binding, the transcriptional activity of a target gene (i.e., a gene associated with the specific DNA sequence) is enhanced as a function of the ligand bound to the receptor heterodimer.

SUMMARY OF THE INVENTION

The present invention is based on the finding that activation of PPARγ plays a key role in inducing growth arrest by terminal differentiation of actively proliferating PPARγ-expressing cells, particularly transformed adipose precursor cells.

Accordingly, one aspect of the invention provides a method for inhibiting proliferation of a PPARγ-responsive hyperproliferative cell, comprising contacting the cell with a PPARγ agonist in an amount effective to induce differentiation of the cell. For example, the instant method can be used for the treatment of, or prophylactically prevention of a disorder characterized by aberrant cell growth of PPARγ-responsive hyperproliferative cells, e.g., by administering a pharmaceutical preparation of a PPARγ agonist in an amount effective to inhibit growth of the PPARγ-responsive hyperproliferative cells.

In one embodiment, the method of the invention is used in the treatment of sarcomas, carcinomas and/or leukemias. Exemplary disorders for which the subject method can be used alone or as part of a treatment regimen include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In certain embodiments, the method of the invention is be used to treat disorders such as carcinomas forming from tissue of the breast, prostate, kidney, bladder or colon.

In other embodiments, the method of the invention is used to treat hyperplastic or neoplastic disorders arising in adipose tissue, such as adipose cell tumors, e.g., lipomas, fibrolipomas, lipoblastomas, lipomatosis, hibemomas, hemangiomas and/or liposarcomas.

In still other embodiments, the method of the invention is used to treat hyperplastic or neoplastic disorders of the hematopoietic system, e.g., leukemic cancers. In a preferred embodiment, the subject is a mammal, e.g., a primate, e.g., a human.

In preferred embodiments, the PPARγ agonist used in the methods of this invention is a ligand of a PPARγ protein which activates a transcriptional activity of the PPARγ protein. For example, the PPARγ agonist can be a thiazolidinedione, or an analog thereof. Exemplary PPARγ agonists include pioglitazone, troglitazone, ciglitazone, englitazone, BRL49653, and chemical derivatives thereof. In certain preferred embodiments, the PPARγ agonist is represented in the general formula:

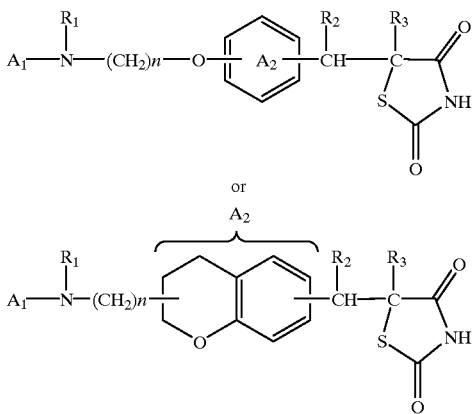

or a tautomeric form thereof, or a pharmaceutically acceptable salt thereof, or a pharmaceutically acceptable solvate thereof, in which $A_1$ represents a substituted or unsubstituted aromatic heterocyclyl group; $R_1$ represents a hydrogen atom, an alkyl group, an acyl group, an aralkyl group, wherein the aryl moiety may be substituted or unsubstituted, or a substituted or unsubstituted aryl group; $R_2$ and $R_3$ each represent hydrogen, or $R_2$ and $R_3$ together represent a bond; $A_2$ represents a benzyl or chromanyl moiety having, as valence permits, up to five substituents; and n represents an integer in the range of from 1 to 6.

In other embodiments, the PPARγ agonist can be a naturally-occurring ligand of the receptor, such as an arachidonate metabolite, e.g., a metabolite of $PGD_2$.

In order to avoid or minimize certain unwanted side-effects to treatment with a PPARγ agonists, it may be desirable in certain embodiments of the subject method that the PPARγ agonist activates PPARγ-dependent transcription at a concentration at least one order of magnitude less than required for the same level of activation of PPARα, PPARδ or RaR-dependent transcription.

The PPARγ agonist can be administered alone, or with another agent as part of a therapeutic regimen therapy. For example, the PPARγ agonist can be conjointly administered with one or more agents such as mitotic inhibitors, alkylating agents, antimetabolites, nucleic acid intercalating agents, topoisomerase inhibitors, agents which promote apoptosis, and/or agents which increase immune responses. In other embodiments, the PPARγ agonist can be administered with an RxR agonist. Such RxR agonist can be natural or synthetic retinoids. An exemplary RxR agonist is represented in the general formula:

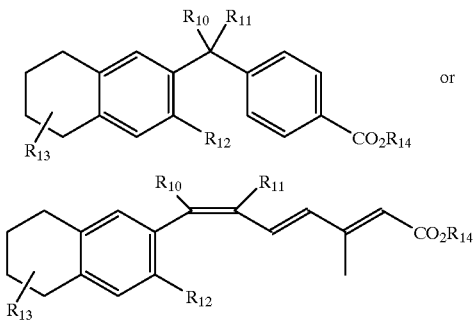

In yet another embodiment, the PPARγ agonist can be administered with a MAP kinase inhibitor. Such an inhibitor can be natural or synthetic agent that specifically blocks MAP kinase activity, e.g., PD098059 (Parke-Davis).

Still another aspect of the present invention provides compositions and kits for administering a at least one PPARγ agonist and an at least one RxR agonist. For example, both agents can be pre-mixed, preferably in a pharmaceutically acceptable carrier. Alternatively, the agents can be provided separately in the form of a kit comprising (i) a first pharmaceutical composition including a PPARγ ligand in a pharmaceutically acceptable carrier, and (ii) a second pharmaceutical composition including an RxR agonist in a pharmaceutically acceptable carrier, the PPARγ ligand and RxR agonist being present in a therapeutically effective amount to, upon administration, induce terminal differentiation of a PPARγ-responsive hyperproliferative cell in a subject animal.

Yet another aspect of the present invention provides compositions and kits for conjointly administering a at least one PPARγ agonist and a at least one MAP kinase inhibitor. For example, both agents can be pre-mixed, preferably in a pharmaceutically acceptable carrier. Alternatively, the agents can be provided separately in the form of a kit comprising (i) a first pharmaceutical composition including a PPARγ ligand in a pharmaceutically acceptable carrier, and (ii) a second pharmaceutical composition including a MAP kinase inhibitor in a pharmaceutically acceptable carrier, the PPARγ ligand and MAP kinase inhibitor being present in a therapeutically effective amount to, upon conjoint administration, induce terminal differentiation of a PPARγ-responsive hyperproliferative cell in a subject animal.

Likewise, the PPARγ agonist useful in the methods of the present invention can be administered with other agents which effect, e.g., the growth of, or immune response against, the hyperproliferative cells to be treated. As above, the secondary agents can be pre-mixed with the PPARγ agonist, or provided as part of a kit comprising (i) a first pharmaceutical composition including a PPARγ ligand in a pharmaceutically acceptable carrier, and (ii) one or more additional pharmaceutical composition(s) including one or more agents selected from the group consisting of mitotic inhibitors, alkylating agents, antimetabolites, nucleic acid intercalating agents, topoisomerase inhibitors, agents which promote apoptosis, and agents which increase immune responses to tumors.

This invention also relates to the surprising discovery that PPARγ is consistently and selectively expressed in each of the major histologic types of human liposarcoma compared to other soft tissue sarcomas. Accordingly, another aspect of the present invention provides a method for diagnosing or augmenting the diagnosing of liposarcomas, comprising detecting in a sample of transformed cells one or both of a diagnostic level of PPARγ mRNA or PPARγ protein, wherein elevated expression of PPARγ mRNA or protein in cells of the sample indicates the presence of liposarcoma cells in the sample. For example, the diagnostic assay can be carried out on a biopsy obtained from a soft tissue hyperplasia or neoplasia.

This invention also relates to the surprising discovery that PPARγ is consistently and selectively expressed in human breast adenocarcinomas and advanced metastatic breast tumors. Accordingly, another aspect of the present invention provides a method for diagnosing or augmenting the diagnosis of breast cancer, comprising detecting in a sample of transformed cells one or both of a diagnostic level of PPARγ mRNA or PPARγ protein, wherein elevated expression of PPARγ mRNA or protein in cells of the sample indicates the presence of adenocarcinoma cells in the sample. For example, the diagnostic assay can be carried Out on a biopsy obtained from a soft tissue hyperplasia or neoplasia.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning, A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

Other features and advantages of the invention will be apparent from the following detailed description, and from the claims.

DETAILED DESCRIPTION OF THE DRAWINGS

FIG. 1 is a panel of photographs showing the effects of pioglitazone in stimulating growth arrest and adipose differentiation of NIH-3T3 cells ectopically expressing PPARγ (NIH-PPARγ) compared to control cells infected with the empty vector (NIH-vector). Arrow shows a differentiated adipocyte containing lipid drops in the cytoplasm.

FIGS. 2A, 2B and 2C show graphs depicting the growth of NIH-PPARγ, NIH-vector or HIB1B cells in the presence or absence of PPARγ ligands. FIG. 2A is a graph depicting the cumulative growth of cells untreated or treated with 5 μM pioglitazone. FIG. 2B is a bar graph showing the percent decrease in cell number in the pioglitazone-treated plates relative to the untreated plates. FIG. 2C is a bar graph showing exponentially growing cells treated without or with two thiazolidinediones, pioglitazone (5 μM) or BRL49653 (1 μM) for 5 days.

FIG. 3 is a bar graph showing the effects of transcription factor activity of PPARγ on the negative regulatory function of cell growth. The left panel shows schematic representations of wild type PPARγ1 and 2, or mutant PPARγ2 cDNAs. The right panel shows the effects of pioglitazone treatment on the growth rate of cells expressing wild type or mutant forms of PPARγ treated with or without pioglitazone.

FIG. 4 shows Northern analysis of RNA prepared from a variety of human tissues. As indicated to the left of the figure, the blot was hybridized with cDNA for PPARγ and for the adipocyte-specific binding protein aP2.

FIG. 5A shows Northern analysis of the expression of PPARγ RNA in RNA prepared from a variety of liposarcomas (SP107, SP144, SP147, SP154, SP158, SP160, SP 115, SP155, SP156, SP200, SP204, SP116). RNAs prepared from fat and muscle tissues are shown as controls. The blot was hybridized with PPARγ cDNA.

FIG. 5B shows Northern analysis of the expression of PPARγ RNA in two liposarcomas (SP155 and SP156) compared to a variety of other types of soft tissue sarcomas which include malignant fibrous histiocytoma (MFH), leiomyosarcoma, angiosarcoma, malignant peripheral nerve sheath tumor (MPNS) or malignant fibrous histiocytoma (MFH). RNA prepared from fat tissue is shown as a control. The blot was hybridized with PPARγ cDNA.

FIG. 6 is a graph depicting the relative potencies of the thiazolidinedione compounds in inducing the expression in CV-1 cells of a reporter plasmid containing the GAL4 upstream activating sequence co-expressed with a fusion expression plasmid having the yeast GAL4 DNA binding domain linked to the ligand binding domain of h PPARγ. The level of activation is indicated with respect to the concentration of the thiazolidinedione compounds, BRL 49653 (shown by filled circles), pioglitazone (shown by unfilled circles) and troglitazone (shown by filled squares).

FIG. 7 is a panel of photographs showing primary cultures of liposarcoma cells cultured in the absence (panels A, C and E) and in the presence of the PPARγ ligand pioglitazone (panels B, D and F). Panels A and B represent untreated and treated cells, respectively; panels C and D represent untreated and treated cells, respectively; and panels E and F represent untreated and treated cells, respectively.

FIG. 8 is a Northern analysis showing the expression of adipocyte-specific markers in untransfected NIH cells (NIH-vector), NIH cells that express PPARγ from a retroviral vector (NIH-PPARγ) and human liposarcoma cells (LS 857). Indicated are untreated cultures (−) and cultures treated with pioglitazone alone (pio), the RXR-specific ligand, LG 268, or both. As indicated to the left, the blot was hybridized with PPARγ, aP2 and adipsin.

Figure 15:
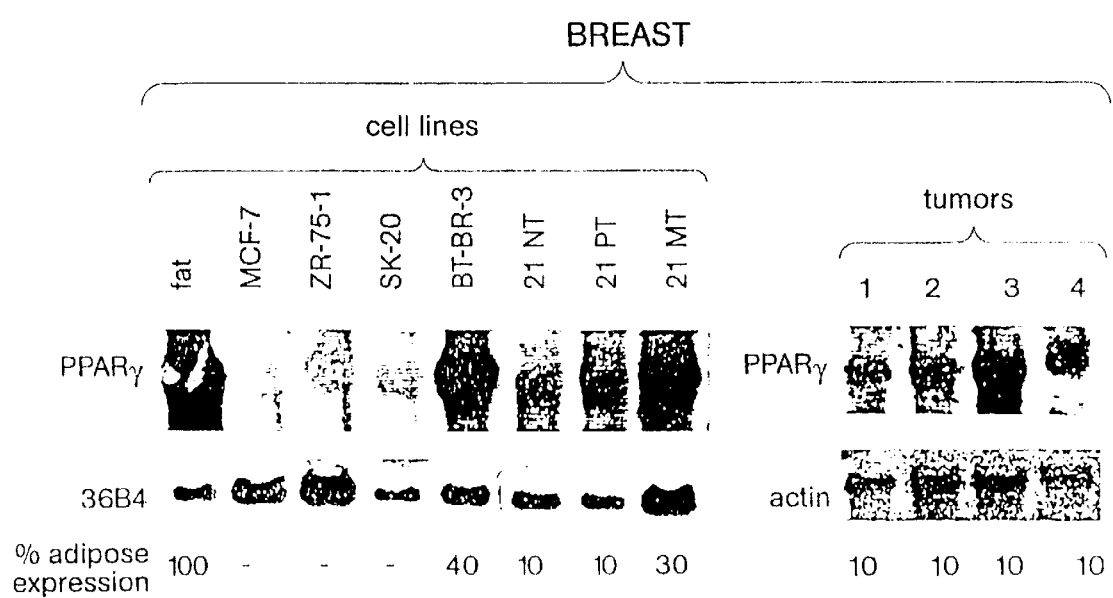

FIG. 15 is a Northern analysis demonstrating the PPARγ mRNA expression in breast cancer cell lines and tumors. Northern blot analysis of breast cell lines and tumors was performed with 30 μg of total RNA per lane. A sample of mRNA from human fat is shown for comparison. Hybridization to cDNA probes for PPARγ, 36B4 and actin were done as described in methods.

FIG. 16 shows immunocytochemical staining of metastatic breast cancer and normal breast tissue with antibody against PPARγ. Consecutive sections were stained either with heamatoxilin and eosin or with PPARγ rabbit antibody at a dilution of 1:1000. Panels a and b show an histologic section of a metastatic breast adenocarcinoma to lung stained with haematoxylin-eosin (a) or PPARγ antibody (b).

Note the intense brown nuclear staining of the metastatic adenocarcinoma cells (arrow 1) and the brown nuclear staining of lung pneumocytes (arrow 2). Panels c and d show an histologic section of normal breast tissue stained with haematoxylin and eosin (c) or PPARγ antibody (d). Note the intense brown nuclear staining of the surrounding normal fat cells (arrow 4).

FIG. 17 shows lipid accumulation in breast cancer cells induced by PPARγ ligands. Staining for lipids was performed with Oil red O (a,c) or by Nile Red fluorescent dye (b). Neutral lipid stains with Oil Red O and yellow with Nile Rad. a. 21PT cells were treated with 10 μM pioglitazone or troglitazone or vehicle for 7 days. b. 21PT cells were treated with 10 μM M2 compound, an inactive metabolite of troglitazone with no affinity for PPARγ, 10 μM troglitazone or 5 μM 15 deoxyΔ $^{12,14}$PGJ$_2$ for 5 days. C. 21MT cells treated with 10 μM pioglitazone, troglitazone or vehicle for 15 days.

FIG. 18 shows the effects of PPARγ activation on growth and gene expression of 21PT breast cancer cells. (a) Northern blot analysis of RNA from 21PT cells treated for 7 days in with pioglitazone (10 μM), LG268 (100 nM) or with the combination of pioglitazone and IG268, or vehicle alone. 30 μg of total RNA were loaded per lane. (b) Incorporation of thymidine in cells that were exponentially growing, when exposed to 10 μM pioglitazone or troglitazone for 3 or 7 days. Cells were then incubated with 2μ Ci/ml of $^3$H-thymidine for a further 24 hours with troglitazone, pioglitazone or vehicle. Error bars represent the standard deviation. (c) Clonogenic assay in cells treated first with troglitazone or vehicle for 15 days (see methods) and then replated at 10$^4$ cells per 10 cm dish, in the presence or absence of troglitazone (10 μM). Cells exposed to troglitazone show a reduction in clonal growth.

FIG. 19 shows MAP kinase inhibition potentiates the ligand activation of PPARγ in 21MT cells. (a) Oil Red O staining for lipid accumulation and (b) Northern blot analysis of mRNAs. 21MT cells were treated for 7 days with 10 μM troglitazone, 4 μM MEK inhibitor PD098059 or the combination of both. (c) Western blot analysis of protein extracts from cells cultured with 10 μm troglitazone, with 40 μM MEK inhibitor PD098059, with the combination of both or vehicle for four hours. The antibody against MAP kinase was specifically prepared to recognize only the phosphorylated, activated forms of this enzyme. The antibody against PPARγ recognizes both the faster migrating, unphosphorylated for (−) and the slower migrating, phosphorylated form (P).

DETAILED DESCRIPTION OF THE INVENTION

Induction of terminal differentiation represents a promising alternative to conventional chemotherapy of certain malignancies. The principle known as "differentiation therapy" is based on the observation that cancer cells appear to be arrested in an immature stage of development. It has been demonstrated that certain tumor cells can be induced to terminally differentiate, both *in vitro* and *in vivo*, into cells which do not proliferate as rapidly as the untreated tumor cell, e.g., which revert to an apparent quiescent phenotype. One group of agents known to induce terminal differentiation of cells are retinoids. The retinoic acid receptor α(RARα), which plays an important role in the differentiation and malignant transformation of cells of the myelocytic lineage, has been used as a target for intervention in acute promyelocytic leukemia (APML) (Warrell, R.P. et al., (1993) N. Engl. J. Med. 329:177–189). Differentiation therapy with all-trans retinoic acid has become the standard of care for this disease.

According to the present invention, receptors of the peroxisome proliferator-activated receptor (PPAR) family also represent targets for differentiation therapy. As described in greater detail herein, agonists of the PPARγ sub-family can be used to inhibit the proliferation of a variety of hyperplastic and neoplastic tissues. In accordance with the present invention, PPARγ agonists can be used in the treatment of both pathologic and non-pathologic proliferative conditions characterized by unwanted growth of PPARγ-responsive cells. Such conditions include tissue having transformed cells, e.g., such as carcinomas, sarcomas, leukemias, as well as, advanced metastatic breast tumors.

Liposarcomas are second in frequency only to malignant fibrous histiocytoma among the soft-tissue sarcomas. Liposarcomas arise from transformed adipose precursor cells. These tumors are the most common soft tissue malignancy in adults, accounting for at least 20% of all sarcomas in this age group. Liposarcoma tumors occur most often in the extremities, particularly in the thigh and retroperitoneum. Three major histologic classifications of liposarcoma are recognized: well differentiated/dedifferentiated, myxoid/round cell, and pleomorphic. Surgery, including amputation of afflicted limbs, remains the primary mode of therapy for localized disease. Metastatic liposarcoma is associated with an extremely poor prognosis, with average five year survivals ranging from 70% to 25% depending on the type of tumor. Conventional chemotherapy for metastatic liposarcoma leads to complete response in only about 10% of cases, and for most patients it is largely palliative. (Sreekantaiah et al. (1994) *Am. J. Pathol.* 144:1121–1134).

Cancer of the breast accounts for more deaths among American women than any other malignancy. Current therapy for primary breast cancer includes surgical resection with or without radiation or chemotherapy depending on the extent of the disease. Conventional adjuvant chemotherapy is suboptimal for two major reasons: it is associated with significant toxicity and it may benefit only 20–25% of patients. For advanced metastatic breast cancer standard cytotoxic chemotherapy is mainly palliative causing only slight improvement in survival rate.

In one aspect, clinical and experimental evidence indicates that differentiation and malignancy in adipocytic cells is inversely correlated. In particular, therapeutic treatment of malignant transformations of adipose lineage cells as, for example, in the treatment of liposarcomas, can be carried out by inducing terminal adipocytic differentiation with an agent (s) that causes activation of transcriptional complexes which include PPARγ. The method of the present invention is based in part on the unexpected finding that administration of PPARγ agonists, such as the synthetic thiazolidinedione ligands (TZDs), is effective in reducing the size of adipose cell tumors in vivo. As described in the appended examples, activation of PPARγ is shown to be sufficient to cause cell cycle arrest, as well as to initiate adipogenesis, in logarithmically growing cells. In addition, PPARγ is shown to be expressed consistently in each of the major histologic types of human liposarcoma, and in adenocarcinomas from breast cancer cells. Activation of this receptor with ectopically added receptor ligand is shown to promote terminal differentiation of primary liposarcoma cells in vitro and in vivo.

The method of the present invention is also based in part on the finding that inhibition of MAP kinase, shown previously to be a powerful negative regulator of PPARγ, improves the TZD ligand sensitivity of relatively non-responsive cells, suggesting that this enzyme can interfere with the function of PPARγ. Furthermore, it has been demonstrated that ligand activation of this receptor in cultured cells derived from both primary and metastatic human breast tumors causes a dramatic morphological conversion with extensive lipid accumulation. In addition, there are changes in breast epithelial gene expression associated with a more differentiated, less malignant state. Coincident with these changes in morphology and gene expression, there is a reduction in growth rate and clonogenic capacity of the cells. Taken together, PPARγ ligands and MAP kinase inhibitors can induce terminal differentiation of malignant breast epithelial cells and thus provide a novel, non-toxic therapy.

In addition to soft tissue lesions, PPARγ agonists can also be used opportunely in the treatment of proliferative disorders involving hematopoietic and lymphatic tissue, as well as certain solid tissue proliferative disorders. The appended examples describe the expression of PPARγ in cells derived from a variety of carcinomas and leukemias. Moreover, PPARγ agonists have been demonstrated to be capable of inhibiting the proliferation of such cells, and have accordingly established a general paradigm by which growth of PPARγ-responsive hyperproliferative cells can be regulated.

RXR-specific ligands have also been demonstrated to be potent adipogenic agents in cells expressing the PPARγ/RXRα heterodimer, and that treatment of liposarcoma cells with both PPARγ- and RXR-specific ligands results in an additive stimulation of differentiation. These results indicate that PPARγ ligands such as thiazolidinediones and RXR-specific retinoids alone or in combination are useful as differentiation therapy for liposarcoma.

Before further description of the invention, certain terms employed in the specification, examples and appended claims are, for convenience, collected here.

The term "PPARγ" refers to members of the peroxisome proliferator-activated receptors family which are expressed, inter alia, in adipocytic and hematopoietic cells (Braissant, O. et al. *Endocrinology* 137(1): 354–66), and which function as key regulators of differentiation. Contemplated within this definition are variants thereof, as for example, PPARγ1 and PPARγ2 which are two isoforms having a different N-terminal generated by alternate splicing of a primary RNA transcript (Tontonoz, P. et al. (1994), *Genes & Dev.* 8:1224–34; Zhu et al. (1993)*J. Biol. Chem.* 268: 26817–20).

The terms "PPARγ-responsive hyperproliferative cell" and "PPARγ-responsive neoplastic cell" are used interchangeably herein and refer to a neoplastic cell which is responsive to PPARγ agonists. This neoplastic cell responds to PPARγ receptor activation by inhibiting cell proliferation and/or inducing the expression of differentiation-specific genes. This term includes tumor-derived cells that differentiate into adipocytic lineages in response to PPARγ ligands, e.g., human liposarcoma cells.

As used herein, a "PPARγ agonist", that is useful in the method of the invention, refers to an agent which potentiates, induces or otherwise enhances the transcriptional activity of a PPARγ receptor in a neoplastic cell. In certain embodiments, an agonist may induce activation of transcription by PPARγ transcriptional complexes, e.g., such as by mimicking a natural ligand for the receptor. In other embodiments, the agonist potentiates the sensitivity of the receptor to a PPARγ ligand, e.g., treatment with the agonist lowers the concentration of ligand required to induce a particular level of receptor-dependent gene activation.

As used herein, the term "PPARγ ligand", that is useful in the method of the invention, includes any naturally-occurring or non-naturally occurring agent that selectively and specifically binds to a PPARγ protein and upon binding, activates transcription of genes which contain a PPARγ responsive element. Examples of such ligands include, but are not limited to thiazolidinedione compounds, e.g., pioglitazone, troglitazone, BRL49653, and derivatives thereof, or prostaglandin (PG) metabolites, e.g., prostaglandin 15-deoxy-$\Delta^{12,14}$ PGJ$_2$, and derivatives thereof.

The term "MAP kinase inhibitor" is used herein to denote any agent that specifically blocks MAP kinase activity, e.g., PD980-59.

The term "agent" is used herein to denote a chemical compound, a mixture of chemical compounds, a biological macromolecule, or an extract made from biological materials such as bacteria, plants, fungi, or animal (particularly mammalian) cells or tissues. Agents can be evaluated for activity as antiproliferative agents by use of a screening assay as described, for example, herein below.

The term "activation of PPARγ" refers to the ability of a compound to selectively activate PPARγ-dependent gene expression, e.g., by increasing PPARγ-dependent transcription of a gene.

The "transcriptional activity" of a PPARγ receptor refers to the ability of the receptor, in a ligand-dependent manner, to bind to DNA and, by itself or in complex with other factors, cause activation of RNA polymerase in order to cause transcription of DNA sequences proximate the site on the DNA to which the PPARγ receptor bound. A PPARγ receptor is "transcriptionally activated" when, in a ligand complexed state it causes a higher level of expression of a gene than in the absence of ligand.

The common medical meaning of the term "neoplasia" refers to "new cell growth" that results as a loss of responsiveness to normal growth controls, e.g. to neoplastic cell growth. A "hyperplasia" refers to cells undergoing an abnormally high rate of growth. However, as used herein, the terms neoplasia and hyperplasia can be used interchangeably, as their context will reveal, referring generally to cells experiencing abnormal cell growth rates. Neoplasias and hyperplasias include "tumors," which may be either benign, premalignant or malignant.

As used herein, the terms "hyperproliferative" and "neoplastic" are used interchangeably, and refer to those cells an abnormal state or condition characterized by rapid proliferation or neoplasm. The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth.

The term "adipose cell tumor" refers to all cancers or neoplasias arising from cells of adipocytic lineage, e.g., arising from adipose or adipose precursor cells. The adipose cell tumors include both common and uncommon, benign and malignant lesions, such as lipoma, intramuscular and intermuscular lipoma, neural fibrolipoma, lipoblastoma, lipomatosis, hibernoma, hemangioma and liposarcoma, as well as lesions that may mimic fat-containing soft-tissue masses.

The term "carcinoma" is recognized by those skilled in the art and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is recognized by those skilled in the art and refers to malignant tumors of mesenchymal derivation.

As used herein the term "leukemic cancer" refers to all cancers or neoplasias of the hemopoietic and immune systems (blood and lymphatic system). The acute and chronic leukemias, together with the other types of tumors of the blood, bone marrow cells (myelomas), and lymph tissue (lymphomas), cause about 10% of all cancer deaths and about 50% of all cancer deaths in children and adults less than 30 years old. Chronic myelogenous leukemia (CML), also known as chronic granulocytic leukemia (CGL), is a neoplastic disorder of the hematopoietic stem cell.

The term "leukemia" is recognized by those skilled in the art and refers to a progressive, malignant disease of the blood-forming organs, marked by distorted proliferation and development of leukocytes and their precursors in the blood and bone marrow.

The terms "antineoplastic agent" and "antiproliferative agent" are used interchangeably herein and refer to agents that have the functional property of inhibiting the proliferation of PPARγ-responsive cells, e.g., inhibiting the development or progression of a neoplasm having such a characteristic, particularly an adipocytic neoplasm or hematopoietic neoplasm.

As used herein, a "therapeutically effective antineoplastic amount" of a PPARγ agonist refers to an amount of an agent which is effective, upon single or multiple dose administration to the patient, at inhibiting the growth of neoplastic PPARγ-responsive cells, or in prolonging the survival of the patient with such neoplastic cells beyond that expected in the absence of such treatment. As used herein, "inhibiting the growth" of the neoplasm refers to slowing, interrupting, arresting or stopping its growth and metastases and does not necessarily indicate a total elimination of the neoplastic growth.

As used herein, "a prophylactically effective antineoplastic amount" of a compound refers to an amount of a PPARγ agonist which is effective, upon single- or multiple-dose administration to the patient, in preventing or delaying the occurrence of the onset or recurrence of a neoplastic disease state.

The term "proliferative index" is recognized by those skilled in the art and refers to the rate at which cell division occurs.

The terms "induce", "inhibit", "potentiate", "elevate", "increase", "decrease" or the like, e.g., which denote quantitative differences between two states, refer to at least statistically significant differences between the two states. For example, "an amount effective to inhibit growth of the PPARγ-responsive hyperproliferative cells" means that the rate of growth of the cells will at least statistically significantly different from the untreated cells. Such terms are applied herein to, for example, rates of cell proliferation, levels of expression, and levels transcriptional activity.

"Signal transduction of a PPARγ receptor protein" is the intracellular processing of chemical signals that occur as a consequence of activation of the nuclear receptor, and may occur through one or more of several mechanisms, such as ligand binding, heterodimer complex formation, DNA binding and/or direct or indirect activation of transcription. Changes in the signal transduction pathway are ultimately detected by the increased expression of differentiation-specific genes and/or withdrawal from the cell cycle.

As used herein, a "reporter gene construct" is a nucleic acid that includes a "reporter gene" operatively linked to a transcriptional regulatory sequences. Transcription of the reporter gene is controlled by these sequences. Typically, the reporter gene construct will include a reporter gene in operative linkage with one or more responsive elements arranged as direct repeats of PPARγ-response element (PPRE). The activity of at least one or more of these control sequences is directly regulated by the PPARγ nuclear receptor protein. The transcriptional regulatory sequences include the promoter and other regulatory regions, such as enhancer sequences, that modulate the activity of the promoter. For example, activation of the high affinity heterodimer complex of PPARγ/RxR with a PPARγ ligand bound to at least one or more PPRE response elements may enhance the activity of the promoter by altering the RNA polymerase binding to the promoter region, or alternatively, by enhancing initiation of transcription or elongation of the mRNA.

I. Methods for inhibiting the proliferation of PPARγ-responsive hyperproliferative cells In one aspect, this invention features methods for inhibiting the proliferation and/or reversing the transformed phenotype of PPARγ-responsive hyperproliferative cells by contacting the cells with a PPARγ agonist. In general, the method includes a step of contacting pathological hyperproliferative cells with an amount of a PPARγ agonist effective for promoting the differentiation of the hyperproliferative cells. The present method can be performed on cells in culture, e.g., in vitro or ex vivo, or can be performed on cells present in an animal subject, e.g., as part of an in vivo therapeutic protocol. The therapeutic regimen can be carried out on a human or other animal subject. Induction of terminal differentiation of transformed cells in vivo in response to PPARγ agonists represents an alternative to conventional highly toxic regimens of chemotherapy.

While the PPARγ agonists can be utilized alone, the subject differentiation therapy can be combined with other therapeutics, e.g., such as cell cycle inhibitors, agents which promote apoptosis, agents which strengthen the immune response, RxR agonists, and/or MAP kinase inhibitors. Some of the co-administered therapeutics, in particular those with cytotoxic effects or which lack specificity for the treated cells, may be given in smaller doses due to an additive, and sometimes synergistic effect with the PPARγ agonist.

In one embodiment, the cells to be treated are hyperproliferative cells of adipocytic lineage, e.g., arising from adipose or adipose precursor cells. For example, the instant method can be carried out to prevent the proliferation of an adipose cell tumor. The adipose tumor cells can be of a liposarcoma. The term "liposarcoma" is recognized by those skilled in the art and refers to a malignant tumor characterized by large anaplastic lipoblasts, sometimes with foci of normal fat cells. Exemplary liposarcoma types which are can be treated by the present invention include, but are not limited to, well differentiated/dedifferentiated, myxoid/round cell and pleiomorphic (reviewed in Sreekantaiah, C. et al., (1994) supra).

Another adipose cell tumor which may be treated by the present method include lipomas, e.g., benign fatty tumors usually composed of mature fat cells. Likewise, the method of the present invention can be used in the treatment and/or prophylaxis of lipochondromas, lipofibromas and lipogranulomas. Lipochondroma are tumors composed of mature lipomatous and cartilaginous elements; lipofibromas are lipomas containing areas of fibrosis; and lipogranuloma are characterized by nodules of lipoid material associated with granulomatous inflammation.

The subject method may also be used to inhibit the proliferation of hyperplastic/neoplastic cells of hematopoietic origin, e.g., arising from myeloid, lymphoid or erythroid lineages, or precursor cells thereof. For example, the present invention encompasses the treatment of various myeloid disorders including, but not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267–97). Lymphoid malignancies which may be treated by the subject method include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas contemplated by the treatment method of the present invention include, but are not limited to, non-Hodgkin's lymphoma and variants thereof, peripheral T-cell lymphomas, adult T-cell leukemia/lymphoma (ATL), cutaneous T-cell lymphoma (CTCL), large granular lymphocytic leukemia (LGF) and Hodgkin's disease.

The subject method can also be used in treating malignancies of the various organ systems, such as those affecting lung, breast, lymphoid, gastrointestinal, and genito-urinary tract as well as adenocarcinomas which include malignancies such as most colon cancers, renal-cell carcinoma, prostate cancer and/or testicular tumors, non-small cell carcinoma of the lung, cancer of the small intestine and cancer of the esophagus. According to the general paradigm of PPARγ involvement in differentiation of transformed cells, exemplary solid tumors that can be treated according to the method of the present invention include sarcomas and carcinomas with PPARγ-responsive phenotypes, such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Particular examples of a non-naturally occurring PPARγ ligand include thiazolidine (TZD) derivatives known as thiazolidinediones, e.g., proglitazone (also known as AD-4833 and U-72107E), troglitazone (also known as CS-045) (Sankyo) and C1-991 (Parke-Davis), BRL 49653, ciglitazone, englitazone and chemical derivatives thereof. These compounds are conventionally known for the treatment of diabetes. See e.g., U.S. Pat. Nos. 4,812,570; 4,775,687; 4,725,610; 4,582,839; and 4,572,912 for exemplary sources of such compounds. U.S. Pat. No. 5,521,201 and European Patent Applications 0008203, 0139421, 0155845, 0177353, 0193256, 0207581 and 0208420, and *Chem. Pharm. Bull* 30 (10) 3580–3600 relate to thiazolidinedione derivatives, and describe commercial sources/synthetic schemes for a variety of TZD and TZD-like analogs, which may be useful in carrying out the method of the present invention.

Particular examples of naturally-occurring PPARγ ligands include arachidonic acid metabolites, e.g., prostaglandin $J_2$ ($PGJ_2$) metabolites, e.g., 15-deoxy-$\Delta^{12,14}$-prostaglandin $J_2$. Prostaglandin J2 dehydration and isomerization products, including $\Delta^{12}$-$PGJ_2$ and 15-deoxy-$\Delta^{12,14}$-$PGJ_2$ have been shown to occur by incubation of prostaglandin $D_2$ ($PGD_2$) in the presence of human plasma or human serum albumin (Fitzpatrick and Wyvalda (1983) *J. Biol. Chem.* 258:11713–18). $\Delta^{12}$-$PGJ_2$ has been shown to be a significant $PGD_2$ metabolite present in human and monkey urine, indicating that $PGJ_2$ metabolites are also found in vivo (Hirata et al. (1994) *PNAS USA* 91:11192–96).

Other agents for use in the methods of the invention include chemicals that stimulate the endogenous production of arachidonic acid metabolites, when administered systemically or in vitro. Enhanced production of endogenous arachidonic acid metabolites may occur by stimulating at least one of the release of arachidonic acid from precursor glycerophospholipids, the oxygenation of free arachidonic acid by a cyclo-oxygenase enzyme, and the metabolism of prostaglandin $H_2$ to a specific biologically active prostaglandin metabolite (reviewed in Smith, W. (1989) *Biochem. J.*, 259:315–24).

In general, it will be preferable to choose a PPARγ agonist which specifically activates that PPAR isoform relative to, for example, PPARα and/or PPARδ. According to this present invention, specificity for the PPARγ isoform can reduce unwanted side effects, such as PPARα-mediated hepatocarcinogenesis. In particular, the PPARγ agonist of the present method preferably activates PPARγ-dependent transcription at a concentration at least 1 order of magnitude less than that which activates PPARα-dependent transcription, and even more preferably at a concentration at least 2, 3, 4 or 5 orders of magnitude less.

In one embodiment, the PPARγ agonist is represented by the general formula:

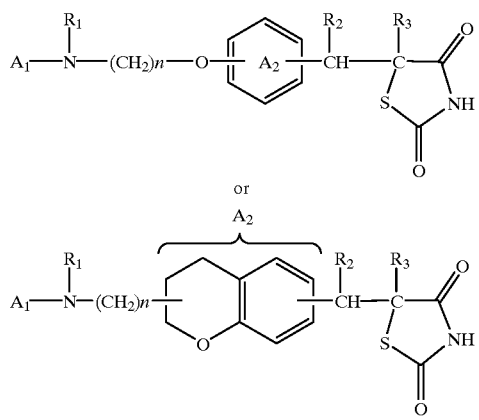

or a tautomeric form thereof and/or a pharmaceutically acceptable salt thereof and/or a pharmaceutically acceptable solvate thereof, in which $A_1$ represents a substituted or unsubstituted aromatic heterocyclyl group; $R_1$ represents a hydrogen atom, an alkyl group, an acyl group, an aralkyl group, wherein the aryl moiety may be substituted or unsubstituted, or a substituted or unsubstituted aryl group; $R_2$ and $R_3$ each represent hydrogen, or $R_2$ and $R_3$ together represent a bond; $A_2$ represents a benzyl or chromanyl moiety having, as valence permits, up to five substituents; and n represents an integer in the range of from 1 to 6.

Suitable aromatic heterocyclyl groups include substituted or unsubstituted, single or fused ring aromatic heterocyclyl groups comprising up to 4 hetero atoms in each ring selected from oxygen, sulphur or nitrogen. Preferred aromatic heterocyclyl groups include substituted or unsubstituted single ring aromatic heterocyclvl groups having 4 to 7 ring atoms, preferably 5 or 6 ring atoms. In particular, the aromatic heterocyclyl group comprises 1, 2 or 3 heteroatoms, especially 1 or 2, selected from oxygen, sulphur or nitrogen.

Suitable substituents for $A_1$ when it represents a 5-membered aromatic heterocyclyl group include thiazolyl and oxazolyl, especially oxazolyl. Suitable substituents for $A_1$ when it represents a 6-membered aromatic heterocyclyl group include pyridyl or pyrimidinyl.

In preferred embodiments, $R_2$ and $R_3$ each represent hydrogen.

Preferably, $A_1$ represents a moiety of formula (a), (b) or (c):

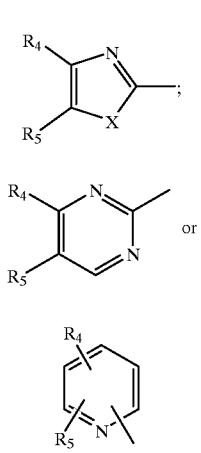

wherein:

$R_4$ and $R_5$ each independently represents a hydrogen atom, an alkyl group or a substituted or unsubstituted aryl group or when $R_4$ and $R_5$ are each attached to adjacent carbon atoms, then $R_4$ and $R_5$ together with the carbon atoms to which they are attached form a benzene ring wherein each carbon atom represented by $R_4$ and $R_5$ together may be substituted or unsubstituted; and in the moiety of formula (a); and X represents oxygen or sulphur.

In one preferred embodiment, $R_4$ and $R_5$ each independently represent hydrogen, alkyl or a substituted or unsubstituted phenyl group and more favorably, $R_4$ and $R_5$ each independently represent hydrogen, alkyl or phenyl. In a further preferred embodiment, $R_4$ and $R_5$ taken together represent a moiety of formula (d):

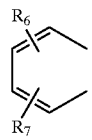

wherein $R_6$ and $R_7$ each independently represent hydrogen, halogen, substituted or unsubstituted alkyl or alkoxy. In preferred embodiments, $R_6$ and $R_7$ represent hydrogen.

Preferably, for the moiety of formula (a), $R_4$ and $R_5$ together represent the moiety of formula (d).

Preferably, for the moieties of formula (b) or (c), $R_4$ and $R_5$ both represent hydrogen.

It will be appreciated that the five substituents of $A_2$ include three optional substituents. Suitable optional substituents for the moiety $A_2$ include halogen, substituted or unsubstituted alkyl or alkoxy.

Preferably, $A_2$ represents a moiety of formula (e):

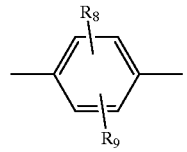

wherein $R_8$ and $R_9$ each independently represent hydrogen, halogen, substituted or unsubstituted alkyl or alkoxy.

In one preferred aspect the present invention provides a class of compounds, which are represented by the general formula:

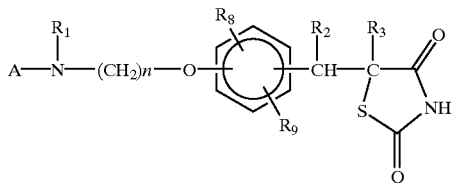

or a tautomeric form thereof, and/or a pharmaceutically acceptable salt thereof and/or a pharmaceutically acceptable solvate thereof, wherein $A_1$, $R_1$, $R_2$, $R_3$, and n are as defined above, and $R_8$ and $R_9$ are as defined in relation to formula (e).

Preferably, n represents an integer 2, 3 or 4, notably 2 or 3 and especially 2.

Suitable substituents for any heterocyclyl group include up to 4 substituents selected from the group consisting of: alkyl, alkoxy, aryl and halogen or any two substituents on adjacent carbon atoms, together with the carbon atoms to which they are attached, may form an aryl group, preferably a benzene ring, and wherein the carbon atoms of the aryl group represented by the said two substituents may themselves be substituted or unsubstituted.

When used herein the term 'aryl' includes phenyl and naphthyl optionally substituted with up to five, preferably up to three, groups selected from halogen, alkyl, phenyl, alkoxy, haloalkyl, hydroxy, amino, nitro, carboxy, alkoxycarbonyl, alkoxycarbonylalkyl, alkylcarbonyloxy, or alkylcarbonyl groups.

When used herein the term 'halogen' refers to fluorine, chlorine, bromine and iodine; preferably chlorine.

When used herein the terms 'alkyl' and 'alkoxy' relate to groups having straight or branched carbon chains, containing up to 12 carbon atoms.

When used herein the term 'acyl' includes alkylcarbonyl groups.

Suitable alkyl groups are C1–12 alkyl groups, especially C1–6 alkyl groups e.g. methyl, ethyl, n-propyl, iso-propyl, n-butyl, isobutyl or tert-butyl groups.

Suitable substituents for any alkyl group include those indicated above in relation to the term "aryl".

Compounds useful for practicing the present invention, and methods of making these compounds are known.

Examples of PPARγ agonists are disclosed in PCT publications WO 91/07107; WO 92/02520; WO 94/01433; WO 89108651; WO 95/18533; WO 95/35108; Japanese patent publication 69383/92; and U.S. Pat. Nos. 5,523,314; 5,521,202; 5,510,360; 5,498,621; 5,496,621; 5,494,927; 5,480,896; 5,478,852; 5,468,762; 5,464,856; 5,457,109; 4,287,200; 4,340,605; 4,438,141; 4,444,779; 4,461,902; 4,572,912; 4,687,777; 4,703,052; 4,725,610; 4,873,255; 4,897,393; 4,897,405; 4,918,091; 4,948,900; 5,002,953; 5,061,717; 5,120,754; 5,132,317; 5,194,443; 5,223,522; 5,232,925; and 5,260,445.

Exemplary PPARγ agonist can be selected from amongst such compounds as 5-[4-[2-(5-ethylpyridin-2-yl)ethoxyl] benzylithiadiazolidine-2,4-dione: (pioglitazone); 5-[4-[(1-methylcyclohexyl)methoxy]benzyl]thiadiazolidine-2,4-dione: (ciglitazone); 5-[(2-benzyl-2,3-dihydrobenzopyran)-5-ylmethyl]thiadiazoline-2,4-dione: (englitazone); 5-[(2-alkoxy-5-pyridyl)methyl]-2,4-thiazolidinedione; 5-[(substituted-3-pyridyl)methyl]-2,4-thiazolidinedione; 5-[4-(2-methyl-2-phenylpropoxy)benzyl]thiazolidine-2,4-dione; 5-[4-[3-(4-methoxyphenyl)-2-oxooxazolidin-5-yl]methoxy]benzyl-2,4-thiazoli-dinedione; 5-[4-[3-(3,4-difluorophenyl)-2-oxooxazolidin-5-yl]-methoxy]benzyl-2,4-thiazo-lidinedione; 5-[4-[3-(4-chloro-2-fluorophenyl)-2-oxooxazolidin-5-yl]methoxy]benzyl-2,4-thiazolidinedione; 5-[4-[3-(4-trifluoromethoxyphenyl)-2-oxooxazolidin-5-yl] methoxy]benzyl-2,4-thiazolidinedione; 5-[4-[3-(4-trifluoromethylphenyl)-2-oxooxazolidin-5-yl]methoxy]benzyl-2,4-thiazolidinedione; 5-[4-[2-[3-(4-trifluoromethylphenyl)-2-oxooxazolidin-5-yl]ethoxy] benzyl]-2,4-thiazolidinedione; 5-[4-[2-[3-(4-chloro-2-fluorophenyl)-2-oxooxazolidin-5-yl]ethoxy]benzyl]-2,4-thiazolidinedione; 5-[4-[3-(4-pyridyl)-2-oxooxazolidin-5-yl]methoxy]-benzyl-2,4-thiazolidinedione; 5-[[4-[(3,4-dihydro-6-hydroxy-2,5,7,8-tetramethyl-2H-1-benzopyran-2-yl)methoxy]phenyl]methyl]-2,4-thiazolidinedione: (troglitazone); 4-(2-naphthylmethyl)-1,2,3,5-oxathiadiazole-2-oxide; 5-[4-[2-N-(benzoxazol-2-yl)-N-methylamino]ethoxy]benzyl]-5-methylthiazolidine-2,4-dione; 5-[4-[2-[2,4-dioxo-5-phenylthiazolidin-3-yl)ethoxy] benzyl]thiazolidine-2,4-dione; 5-[4-[2-[N-methyl-N-(phenoxycarbonyl)amino]ethoxy]benzyl]thiazolidine-2,4-dione; 5-[4-(2-phenoxyethoxy)benzyl]thiazolidine-2,4-dione; 5-[4-[2-(4-chlorophenyl)ethylsulfonyl]benzyl] thiazolidine-2,4-dione; 5-[4-[3-(5-methyl-2-phenyloxazol4-yl)propionyl]benzyl]thiazolidine-2,4-dione; 5-[[4-(3-hydroxy-1-methylcyclohexyl)methoxy]benzyl] thiadiazolidine-2,4-dione; 5-[4-[2-(5-methyl-2-phenyloxazol-4-yl)ethoxyl]benzyl]thiadizolidione-2,4-dione; 5-[[2-(2 -naphthylmethyl)benzoxazol]-5-ylmethyl] thiadiazoline-2,4-dione; 5-[4-[2-(3-phenylureido)ethoxyl] benzyl]thiadiazoline-2,4-dione; 5-[4-[2-[N-(benzoxazol-2-yl)-N-methylamino]ethoxy]benzy]thiadiazoline-2,4-dione; 5-[4-[3-(5-methyl-2-phenyloxazol-4-yl)propionyl]benzyl] thiadiazoline-2,4-dione; 5-[2-(5-methyl-2-phenyloxazol-4-ylmethyl)benzofuran-5-ylmethyl]-oxazolidine-2,4-dione; 5-[4-[2-[N-methyl-N-(2-pyridyl)amino]ethoxy]benzyl] thiazolidine-2,4-dione; and 5-[4-[2-[N-(benzoxazol-2-yl)-N-methylamino]ethoxy]benzyl]-oxazolidine-2,4-dione.

In another embodiment, the subject methods combines the use of PPARγ agonists with one or more RxR-specific ligands. For example, the subject method can be practiced by treatment using a PPARγ agonist as described above and an RxR agonist such as a natural and/or synthetic retinoid. A wide variety of RxR ligands appropriate for use in the subject method are known in the art. Exemplary natural RxR ligands include all-trans-retinoic acid and phytanic acid. Exemplary synthetic RxR ligands include 9-cis-retinoic acid, LG268, AGN191701, SR11217, SR11237, SR11236, SR11246, SR11249 SR11256, LGD1069, various tricyclic retinoids, teravinyl-alkadi- or trienoic derivatives of retinoids, and phenyl-methyl heterocylic and tetrahydro-napthyl analogs of retinoic acid (c.f., Apfel et al. (1995) *JBC* 270:30765; Minucci et al. (1996) *PNAS* 93:1803; Hembree et al. (1996) *Cancer Res* 56:1794; Kizaki et al. (1996) *Blood* 87:1977; Lemotte et al. (1996) *Eur J Biochem* 236:328; and U.S. Pat. Nos. 5,552,271; 5,466,861; 5,514,821; PCT publications WO 96105165; WO 96/20914; WO 94/15901; WO 93/21146; and European Patent publication EP 0694301.

To further illustrate, the RxR ligand can be a compound represented in the general formula:

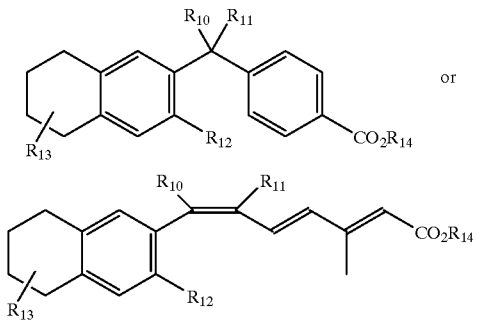

and U.S. Pat. No. 5,466,861.

The two (or more) compounds are administered in combination according to the invention. The term "in combination" in this context means that the drugs are given substantially contemporaneously, either simultaneously or sequentially. If given sequentially, at the onset of administration of the second compound, the first of the two compounds is preferably still detectable at effective concentrations at the site of treatment.

In yet another embodiment, the subject methods combines the use of PPARγ agonists with one or more MAP kinase inhibitors. For example, the subject method can be practiced by treatment using a PPARγ agonist as described above and a MAP kinase inhibitor. An example of such an inhibitor is PD098059.

The subject method may involve, in addition to the use of PPARγ agonist (and optional RxR agonists and/or MAP kinase inhibitors), one or more other anti-tumor substances. Exemplary combinatorial therapies combining with PPARγ agonists include the use of such as agents as: mitotic inhibitors, such as vinblastine; alkylating agents, such as cisplatin, carboplatin and cyclophosphamide; antimetabolites, such as 5-fluorouracil, cytosine arabinoside, hydroxyurea or N-[5-[N-(3,4-dihydro-2-methyl-4-oxoquinazolin-6-ylmethyl)-N-methylamino]-2-thenoyl]-L-glutamic acid; intercalating antibiotics, as for example adriamycin and bleomycin; enzymes, such as asparaginase; topoisomerase inhibitors, such as etoposide; biological response modifiers, e.g., to enhance anti-tumor responses, such as interferon; apoptotic agents, such as actinomycin D; and anti-hormones, for example antioestrogens such as tamoxifen or, for example antiandrogens such as 4'-cyano-3-(4-fluorophenylsulphonyl)-2-hydroxy-2-methyl-3'-(trifluoromethyl) propionanilide. Such conjoint treatment may be achieved by way of the simultaneous, sequential or separate dosing of the individual components of the treatment.

Another aspect of the present invention accordingly relates to kits for carrying out the administration of the PPARγ agonist with other therapeutic compounds. In one embodiment, the kit comprises a PPARγ agonist formulated in a pharmaceutical carrier, and at least one of an RxR agonist, a MAP kinase inhibitor, a mitotic inhibitor, an alkylating agent, an antimetabolite, an nucleic acid intercalating agent, a topoisomerase inhibitor, interferon, formulated with the PPAR-γ agonist or, as appropriate, in one or more separate pharmaceutical preparations.

Determination of a therapeutically effective antineoplastic amount and a prophylactically effective antineoplastic amount of a PPARγ agonist, e.g., the design of the differentiation therapy, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician, the severity of the condition being treated and the particular compound being employed. In determining the therapeutically effective antineoplastic amount or dose, and the prophylactically effective antineoplastic amount or dose, a number of factors are considered by the attending clinician, including, but not limited to: the specific hyperplastic/neoplastic cell involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the PPARγ agonists with other co-administered therapeutics); and other relevant circumstances. U.S. Pat. No. 5,427,916, for example, describes method for predicting the effectiveness of antineoplastic therapy in individual patients, and illustrates certain methods which can be used in conjunction with the treatment protocols of the instant invention.

Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired. A therapeutically effective antineoplastic amount and a prophylactically effective antineoplastic amount of a PPARγ agonist is expected to vary from about 0.1 milligram per kilogram of body weight per day (mg/kg/day) to about 100 mg/kg/day.

Compounds which are determined to be effective for the prevention or treatment of tumors in animals, e.g., dogs, rodents, may also be useful in treatment of tumors in humans. Those skilled in the art of treating tumor in humans will know, based upon the data obtained in animal studies, the dosage and route of administration of the compound to humans. In general, the determination of dosage and route of administration in humans is expected to be similar to that used to determine administration in animals.

The identification of those patients who are in need of prophylactic treatment for hyperplastic/neoplastic disease states is well within the ability and knowledge of one skilled in the art. Certain of the methods for identification of patients which are at risk of developing neoplastic disease states which can be treated by the subject method are appreciated in the medical arts, such as family history of the development of a particular disease state and the presence of risk factors associated with the development of that disease state in the subject patient. The present application also describes other prognostic tests which can be used to make, or to augment a clinical predication about the use of the method of the present invention. A clinician skilled in the art can readily identify such candidate patients, by the use of, for example, clinical tests, physical examination and medical/family history.

II. Pharmaceutical Compositions

In another aspect, the present invention provides pharmaceutically acceptable compositions which comprise a therapeutically-effective amount of one or more of the PPARγ and/or RXR agonists and/or MAP kinase inhibitors, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of a PPARγ and/or RXR agonist (s), material, or composition comprising a compound which is effective for producing some desired therapeutic effect by inhibiting the proliferation and/or inducing the differentiation of at least a sub-population of cells in an animal at a reasonable benefit/risk ratio applicable to any medical treatment.

The phrase "pharmaceutically acceptable" is employed herein to refer to those PPARγ and/or RXR agonists, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of PPARγ and/or RXR agonists. These salts can be prepared in situ during the final isolation and purification of the PPARγ and/or RXR agonists, or by separately reacting a purified PPARγ and/or RXR agonist in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19).

In other cases, the PPARγ agonists useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of a PPARγ and/or RXR agonist(s). These salts can likewise be prepared in situ during the final isolation and purification of the PPARγ and/or RXR agonist(s), or by separately reacting the purified PPARγ and/or RXR agonist(s) in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a PPARγ and/or RXR agonist(s) with the carrier and, optionally, one or more accessory ingredients. In general, the formulations are prepared by uniformly and intimately bringing into association a PPARγ agonist with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a PPARγ and/or RXR agonist(s) as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active PPARγ and/or RXR agonist(s) may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations for rectal or vaginal administration may be presented as a suppository, which may be prepared by mixing one or more PPARγ and/or RXR agonist(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of a PPARγ and/or RXR agonist(s) include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to PPARγ and/or RXR agonist(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a PPARγ and/or RXR agonist(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The PPARγ and/or RXR agonist(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a PPARγ and/or RXR agonist (s) to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more PPARγ and/or RXR agonist(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of PPARγ and/or RXR agonist(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the PPARγ and/or RXR agonist(s) of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of agents may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a PPARγ and/or RXR agent(s), drug or other material other than directly into the central nervous system, such that it enters the patient's system and, thus, is subject to metabolism and other like processes, for example, subcutaneous administration.

These PPARγ and/or RXR agonist(s) may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the PPARγ and/or RXR agonist(s), which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

III. Diagnostic Uses

In yet another aspect, detection of PPARγ RNA and/or protein expression can provide a useful diagnostic method for detecting and/or phenotyping hyperplastic and neoplastic cell disorders. For example, as described in the appended examples, PPARγ is found to be selectively expressed in liposarcomas, in contrast to undetectable levels of expression found in other forms of soft tissue sarcoma such as leiomyosarcoma, fibrosarcoma, angiosarcoma, malignant peripheral nerve sheath tumor (MPNS), or malignant fibrous histiocytoma (MFH) (see FIG. 10B). Thus, PPARγ appears to be a marker for distinguishing adipose cell tumors from other histologic types of soft tissue sarcoma.

In still yet another aspect, detection of PPARγ RNA and/or protein expression can provide a useful diagnostic method for detecting and/or phenotyping breast cancer cell disorders. For example, as described in the appended examples, PPARγ is found to be expressed at significant levels in many human breast adenocarcinomas as well as in a significant proportion of advanced metastatic breast tumors. In addition, inhibition of MAP kinase improves the TZD ligand sensitivity of relatively non-responsive cells, suggesting that this enzyme can interfere with the function of PPARγ, in breast cancer cells.

The amount of specific PPAR-γ RNA or protein may be measured using any method known to those of skill in the art to be suitable. For example, RNA expression may be detected using Northern blots or RNA-based polymerase chain reaction. Specific protein product may be detected by Western blot. Preferably, the detection technique will be quantitative or at least semi-quantitative.

In one embodiment, mRNA is obtained from a sample of cells, and transcripts encoding a PPARγ receptor are detected. To illustrate, an initial crude cell suspension, such as may be obtained from dispersion of a biopsy sample, is sonicated or otherwise treated to disrupt cell membranes so that a crude cell extract is obtained. Known techniques of biochemistry (e.g., preferential precipitation of proteins) can be used for initial purification if desired. The crude cell extract, or a partially purified RNA portion therefrom, is then treated to further separate the RNA. For example, crude cell extract can be layered on top of a 5 ml cushion of 5.7 M CsCl, 10 mM Tris-HCl, pH 7.5, 1 mM EDTA in a 1 in.×3½ in. nitrocellulose tube and centrifuged in an SW27 rotor (Beckman Instruments Corp., Fullerton, Calif.) at 27,000 rpm for 16 hrs at 15° C. After centrifugation, the tube contents are decanted, the tube is drained, and the bottom 0.5 cm containing the clear RNA pellet is cut off with a razor blade. The pellets are transferred to a flask and dissolved in 20 ml 10 mM Tris-HCl, pH 7.5, 1 mm EDTA, 5% sarcosyl and 5% phenol. The solution is then made 0.1 M in NaCl and shaken with 40 ml of a 1:1 phenol:chloroform mixture. RNA is precipitated from the aqueous phase with ethanol in the presence of 0.2 M Na-acetate pH 5.5 and collected by centrifugation. Any other method of isolating RNA from a cellular source may be used instead of this method. Other mRNA isolation protocols, such as the Chomczynski method (described in U.S. Pat. No. 4,843,155), are well known.

The MnRNA must be isolated from the source cells under conditions which preclude degradation of the mRNA. The action of RNase enzymes is particularly to be avoided because these enzymes are capable of hydrolytic cleavage of the RNA nucleotide sequence. A suitable method for inhibiting RNase during extraction from cells involves the use of 4 M guanidium thiocyanate and 1 M mercaptoethanol during the cell disruption step. In addition, a low temperature and a pH near 5.0 are helpful in further reducing RNase degradation of the isolated RNA.

In certain embodiments, the next step may be to form DNA complementary to the isolated heterogeneous sequences of mRNA. The enzyme of choice for this reaction is reverse transcriptase, although in principle any enzyme capable of forming a faithful complementary DNA copy of the mRNA template could be used. The cDNA transcripts produced by the reverse transcriptase reaction are somewhat heterogeneous with respect to sequences at the 5' end and the 3' end due to variations in the initiation and termination points of individual transcripts, relative to the mRNA template. The variability at the 5' end is thought to be due to the fact that the oligo-dT primer used to initiate synthesis is capable of binding at a variety of loci along the polyadenylated region of the mRNA. Synthesis of the cDNA transcript begins at an indeterminate point in the poly-A region, and variable length of poly-A region is transcribed depending on the initial binding site of the oligo-dT primer. It is possible to avoid this indeterminacy by the use of a primer containing, in addition to an oligo-dT tract, one or two nucleotides of the RNA sequence itself, thereby producing a primer which will have a preferred and defined binding site for initiating the transcription reaction.

In an exemplary embodiment, there is provided a nucleic acid composition comprising a (purified) oligonucleotide probe including a region of nucleotide sequence which is capable of hybridizing to a sense or antisense sequence of a PPARγ transcript. The nucleic acid of a cell is rendered accessible for hybridization, the probe is exposed to nucleic acid of the sample, and the hybridization of the probe to the sample nucleic acid is detected. Such techniques can be used to quantitatively determine mRNA transcript levels.

In certain embodiments, detection of the PPARγ transcripts utilizes a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1944) PNAS 91:360–364). In an illustrative embodiment, the method includes the steps of (i) collecting a sample of cells from a patient, (ii) isolating nucleic acid (e.g., mRNA) from the cells of the sample, (iii) contacting the nucleic acid sample (or optionally a cDNA preparation derived therefrom) with one or more primers which specifically hybridize to a PPARγ transcript under conditions such that hybridization and amplification of at least a portion of the transcript (if present) occurs, and (iv) detecting the presence or absence of an amplification product.

Detection and/or amplification can be carried out with a probe which, for example, hybridizes under stringent conditions to a nucleic acid encoding a PPARγ transcript. For detection, the probe preferably further comprises a label group attached to the nucleic acid and able to be detected.

In yet another embodiment, the assay detects the presence or absence of a the PPARγ protein in cells of the cell sample, e.g., by determining the level of the CDK-inhibitory protein by an immunoassay, gel electrophoresis or the like.

IV Drug Screen

In another aspect, the invention features a method for identifying antineoplastic agents which inhibit proliferation of a PPARγ-responsive hyperproliferative cells, e.g., agent which can be used in the above-described method. In any of following drug screening assays, it will be appreciated that selective binding/activation of PPARγ can be assessed by differential screening, e.g., by running a test compound through side-by-side assays which are identical except that PPARγ is replaced by, for example, PPARα, PPARδ, an RxR receptor or the like. Such assays can be used to select compounds which are selective for the PPARγ sub-type of receptor.

In one embodiment, the assay includes the steps of: (i) establishing cultures of PPARγ-responsive hyperproliferative cells; (ii) contacting the transformed cells with a test compound; and (iii) detecting one of proliferation and/or differentiation, wherein compounds are selected by observing a statistically significant decrease in the extent of proliferation (or in the appearance of a differentiated phenotype) in the presence of the test compound. For example, changes in the proliferation of test cells can be assayed by comparing the number of cells labeled with bromo-deoxy uridine (BrdU) in cultures treated with a potential PPARγ agonist compared to untreated controls. The extent of, for example, adipocyte differentiation, for example, can be determined by detecting at least one of changes in cell morphology, accumulation of intracellular lipid, induction of adipocyte-specific genes, e.g., aP2 and adipsin, and/or withdrawal from the cell cycle.

Prior to testing a compound in the cell-based assay, simple binding assays, e.g., using purified or semi-purified PPARγ protein, can be used to isolate those test compounds which at least bind to the receptor. For example, competition binding assays may be performed which comprise incubating the PPARγ receptor protein with a labeled ligand, e.g., [$^3$H]-TZD, in the absence or the presence of an unlabeled test compound; and identifying those compounds that specifically compete off the labeled ligand, wherein a statistically significant difference in the amount of displaced ligand indicates that the test compound binds specifically to PPARγ (see Lehman et al. (1995) J. Biol. Chem. 270:12953–56). Scatchard analysis may be used to determine the extent of ligand binding as commonly used to analyze binding of ligands to thyroid hormone receptors. (Allenby et al. (1993) PNAS USA, 90: 30–4; Banner et al., Annal. Biochem. 200: 163–70). The cell-based assay then provides a functional assay for discerning between agonistic, antagonistic and incidental binding.

In accordance with a still further embodiment of the present invention, there is provided a method for evaluating whether test compounds are PPARγ ligands by detecting the activation of the PPARγ-signaling pathway, comprising (i) establishing a culture of reagent cells which express PPARγ and include a reporter gene construct having a reporter gene which is expressed in an PPARγ-dependent fashion; (ii) contacting the reaget cells with test compounds; and (iii) monitoring the amount of expression of the reporter gene. Expression of the reporter gene reflects transcriptional activity of the PPARγ protein and, therefore, the presence of an activated receptor PPARγ-ligand complex. In an optional yet preferred embodiment, an apparent PPARγ agonist detected by the transcriptional activation assay can then be further tested by contacting that agent with a PPARγ-responsive hyperproliferative cell.

Typically, the reporter gene construct will include a reporter gene in operative linkage with one or more transcriptional regulatory elements responsive to PPARγ, e.g., such as the PPARγ response element (PPRE) known in the art. The amount of transcription from the reporter gene may be measured using any method known to those of skill in the art to be suitable. For example, specific mRNA expression may be detected using Northern blots or specific protein product may be identified by a characteristic stain, immunoassay or an intrinsic activity.

In preferred embodiments, the gene product of the reporter is detected by an intrinsic activity associated with that product. For example, the reporter gene may encode a gene product that, by enzymatic activity, gives rise to a detection signal based on color, fluorescence, or luminescence. The amount of expression from the reporter gene is then compared to the amount of expression in either the same cell in the absence of the test compound or it may be compared with the amount of transcription in a substantially identical cell that lacks the specific receptors. Any statistically or otherwise significant difference in the amount of transcription indicates that the test compound has in some manner altered the activity of the specific receptor.

Alternatively, to establish an assay for PPARγ activity without interference from the endogenous receptor, cells can be constructed that express a chimeric protein having the ligand binding domain of PPARγ fused to a DNA binding protein of a heterologous protein, such as the yeast GAL4 DNA binding domain or the bacterial LexA DNA binding domain. Such constructs are used with a reporter construct containing the GAL4 or LEXA response elements operatively linked to a reporter gene.

After identifying certain test compounds as potential PPARγ agonists, the practioner of the subject assay will continue to test the efficacy and specificity of the selected compounds both in vitro and in vivo. Whether for subsequent in vivo testing, or for administration to an animal as an approved drug, agents identified in the subject assay can be formulated in pharmaceutical preparations, such as described above, for in vivo administration to an animal, preferably a human.

The invention now being generally described, it will be more readily understood by reference to the following examples which are included merely for purposes of illustration of certain aspects and embodiments of the present invention, and are not intended to limit the invention. The contents of all references, patent applications, patents and published patent applications cited throughout this application are hereby incorporated by reference.

Exemplification

EXAMPLE 1

PPARγ Induces Cell Cycle Withdrawal
(i) Experimental Procedures
Cell culture, transfections and plasmids Preparation of the PPARγ2, PPARγ1, PPARγ-M2, PPARγ-M1 viral expression vectors (Tontonoz, P. et al. (1994) supra; Tontonoz, P. et al. (1994) *Cell* 79:1147–56) and 3xwt-E2F-Luciferase (Krek, W. et al. (1993) *Science* 262:1557–60) construct were described previously. The PPARγ2-CD cDNA (encoding amino acids 1–494) was amplified from the PPARγ2 cDNA by PCR and inserted into the pBabe-Puro retroviral expression vector.

Stable cell lines expressing wild type or mutant forms of PPARγ were derived as described (Tontonoz, P. et al. (1994) *Cell* 79:1147–56). BOSC23 cells were cultured in 90-mm dishes and transfected at 80% confluence by calcium-phosphate coprecipitation with 10 μg of pBabe-derived expression vector as described (Pear, W. S. et al. (1993) *PNAS USA* 90:8392–6). 48 hr after transfection viral supernatants were collected and NIH3T3 cells were infected at 50% confluence with equal titers of recombinant virus. The supernatants were applied to the cells in DMEM containing 10% cosmic calf serum (Hyclone) and 4 μg/ml of polybrene. 24 hr after infection, cells were split and plated in DMEM containing 10% calf serum and 2 μg/ml puromycin to select infected cells. NIH-3T3 cell lines infected with empty vector or with viral expression vectors containing wild type or mutant forms of PPARγ cDNA as well as HIB1B and 3T3-F442A cell lines were cultured in DMEM containing 10% cosmic calf serum. Pioglitazone (5-[4-[2-(5-ethyl-2-pyridyl)-ethoxy]benzyl]-2,4-thiazolidinedione) (Upjohn), was dissolved in DMSO and used in cell culture experiments.

RNA and protein analysis

Total RNA was isolated from cultured cells by guanidine isothiocyanate extraction (Chirgwin, J. M. et al. (1979) *Biochemistry* 18:5294–9). RNA, denatured in formamide and formaldehyde was electrophoresed through formaldehyde containing agarose gels as described (Maniatis, T. et al. (1989) Cold Spring Harbor Laboratory Press, Cold Spring Harbor, N.Y.). For Western blot analysis cellular extracts were prepared as described (Maniatis, T. et al. (1989) Cold Spring Harbor Laboratory Press, Cold Spring Harbor, N.Y.) blotted and probed with a appropriate antibody (Upstate Biotech. Inc.).

BrdU incorporation experiments

BrdU incorporation experiment was performed as described in the protocol provided by the supplier (Boehringer Mannheim Biochemical). Briefly, cells grown on coverslips were labeled with 10 μM BrdU for 1 hr. Samples were washed and fixed with ethanol-glycine buffer and incubated with anti-BrdU monoclonal antibody. After incubation with anti-mouse-Ig-alkaline phosphatase followed by the substrate reaction, bound anti-BrdU antibody was visualized by light microscopy.

(ii) Activation of PPARγ leads to cell cycle withdrawal

To study the effect of PPARγ activation on cell growth, we used a retrovirus transfection system to express PPARγ in NIH3T3 cells. This system allows us to express ectopic genes in many thousands of cells at relatively equal levels. PPARγ has two isoforms, PPARγ1 and PPARγ2, that have different N-terminal formed by alternative splicing (Tontonoz, P. et al. (1994) supra; Zhu, Y. et al. (1993) *J. Biol. Chem.* 268:26817–20). NIH3T3 fibroblasts were infected with the retroviral expression vector containing cDNA encoding PPARγ1 or 2 (NIH-PPARγ), or with the empty vector (NIH-vector) to create stable cell lines. NIH-PPARγ cells expressed approximately one-third the level of endogenous PPARγ observed in differentiated adipocytes as determined by Northern analysis (data not shown).

Figure 1:
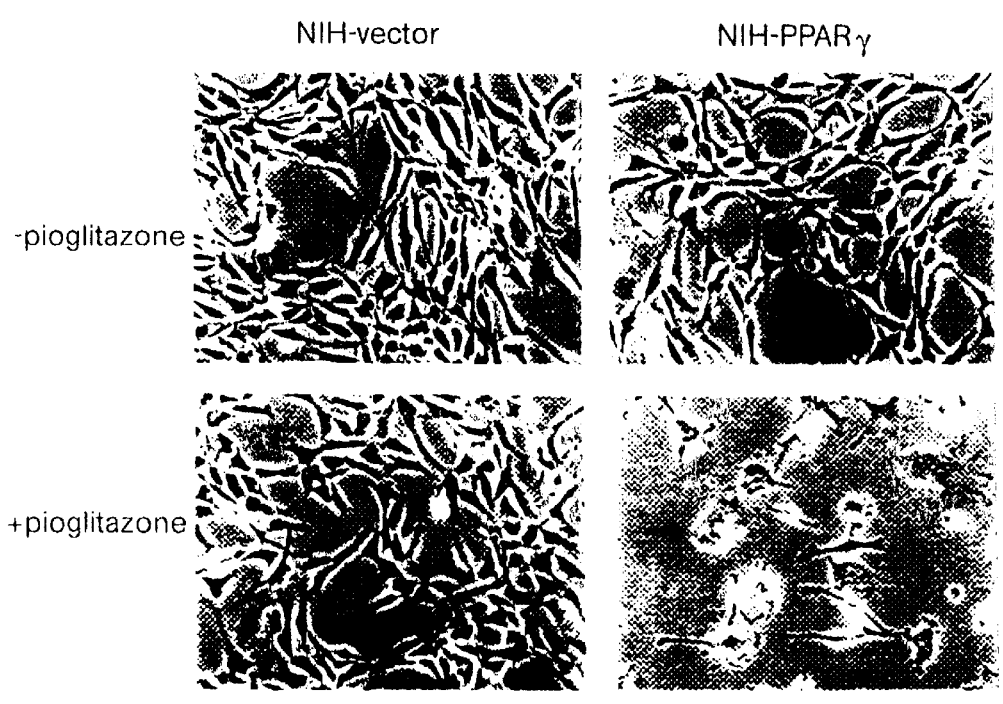

Exponentially growing NIH-PPARγ and NIH-vector cells were treated with a synthetic PPARγ ligand pioglitazone, which belongs to the class of thiazolidinedione antidiabetic agents (Lehmann, J. M. et al. (1995) *J. Biol. Chem.* 270:12953–6). After selection in puromycin, cells were pooled and cultured with or without pioglitazone (5 μM) for 5 days. As shown in FIG. 1, treatment with pioglitazone at 5 μM concentration bad no obvious effect on cells containing empty vectors. In contrast, this agent had dramatic effects on NIB-PPARγ cells, inhibiting cell proliferation and inducing drastic morphological changes. Starting at approximately 48 hours after treatment, increasing numbers of NIH-PPARγ cells changed from the elongated fibroblastic shape to an adipocyte-like morphology, with a round form and accumulation of small drops of lipids within the cytoplasm (FIG. 1, arrow).

Figure 2A:
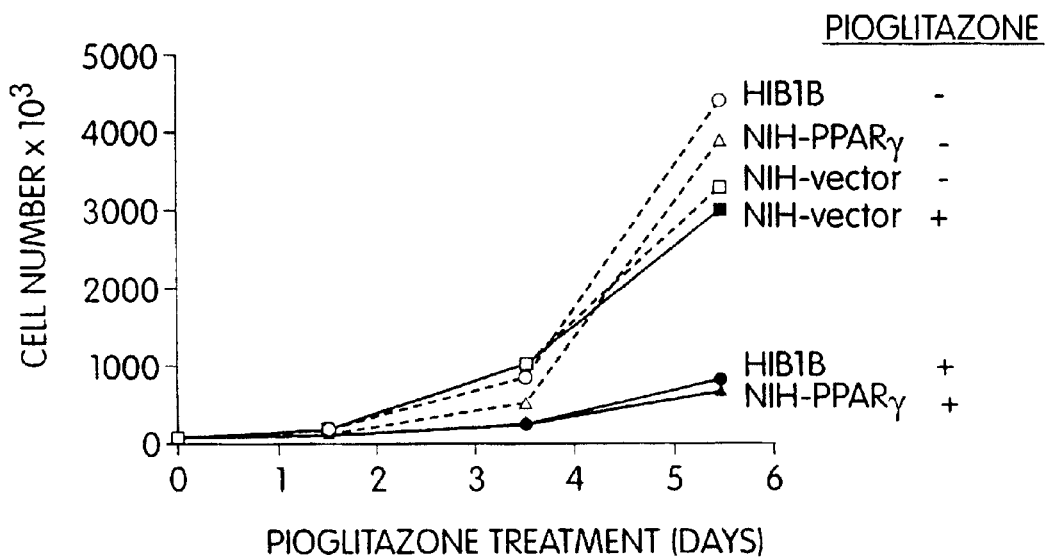
Figure 2B:
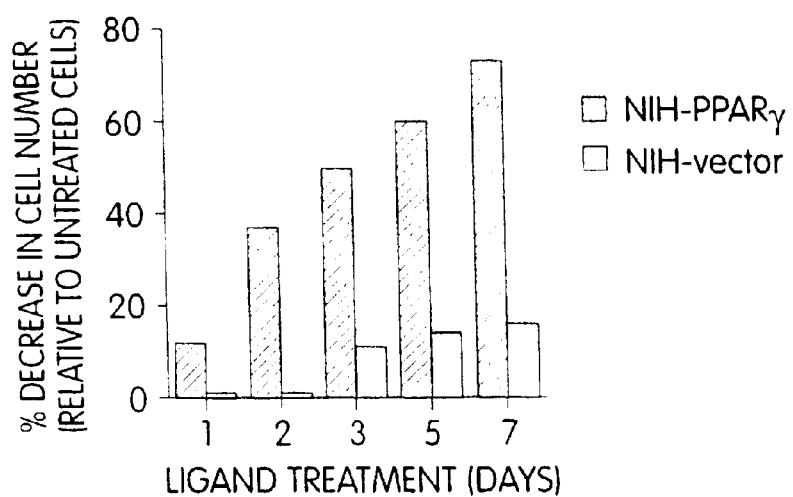
Figure 2C:
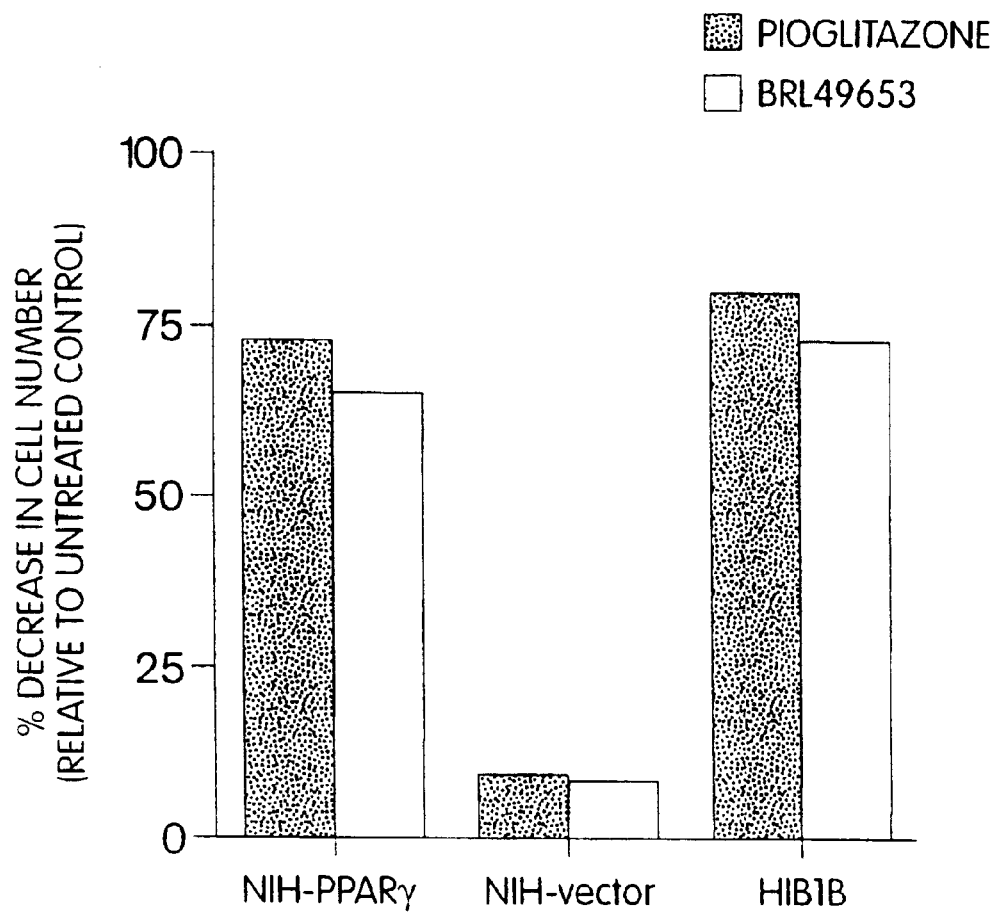

Time course studies at different time points after pioglitazone treatment showed that the number of NIH-PPARγ cells in ligand-treated plates was reduced by almost 40% relative to controls by 2 days after treatment and by 80% after 5 days with pioglitazone (FIGS. 2A, B). The same number of NIH-PPARγ, NIH-vector or HIB1B cells were cultured either in the presence (+) or absence (−) of PPARγ ligands. Cell numbers were determined at the indicated time points. The effect of ligands on cell growth is represented as percentage decrease in cell numbers in the treated plates relative to untreated control plates. The growth of pioglitazone treated NIH-vector cells decreased by 10% over this period compared to untreated control cells, which may be due to the presence of low amount of PPARγ in these cells (data not shown). The addition of 1 μM BRL49653, another synthetic thiazolidinedione ligand of PPARγ (Lehmnann, J. M. et al. (1995) supra) was found to exert the same degree of inhibition on cell growth of NIH-PPARγ cells (FIG. 2C). No obvious cytotoxic effects were observed at the concentrations that we used these compounds.

To analyze whether pioglitazone treatment of cells expressing PPARγ affects progression through a specific cell cycle stage we performed fluorescence activated cell sorting (FACS) analysis and BrdU incorporation experiments. Ligand treatment led to an accumulation of the cell populations in the G0/G1 phase of cell cycle (data not shown). The percentage of cells undergoing DNA synthesis after 5 days of pioglitazone treatment was determined by the ability of cells to incorporate BrdU. As shown in table 1, ligand treatment did not change BrdU incorporation rate in NIH-vector cells, but it caused an 80% decrease in the BrdU incorporation rate in NIH-PPARγ and 3T3-F442A preadipocytes after 5 days of treatment. Together these results demonstrate that ligand activation of PPARγ is sufficient to cause cell cycle withdrawal, even in rapidly proliferating cells. Specifically shown in table 1 are cells cultured on coverslips were untreated or treated with 5 μM pioglitazone for 5 days and then pulsed with BrdU for 1 hour. Coverslips were fixed and processed as described in materials and methods. Cells undergoing DNA synthesis during exposure to BrdU were determined by immunohistochemical staining and considered as BrdU positive. The data represents the average of two independent experiments in which approximately 400 cells were counted per sample.

Table 1: shows the effects of the activation of PPARγ in causing cell cycle withdrawal in normal NIH-PPARγ cells, in F442A preadipocytes and in transformed HIB1 B cells.

|  | pioglitazone | BrdU positive % |
| --- | --- | --- |
| NIH-vector | − | 44 |
| NIH-vector | + | 43 |
| NIH-PPARγ | − | 44 |
| NIH-PPARγ | + | 9 |
| HIB1B | − | 75 |
| HIB1B | + | 11 |
| 3T3-F442A | − | 63 |
| 3T3-F442A | + | 14 |

Figure 3:
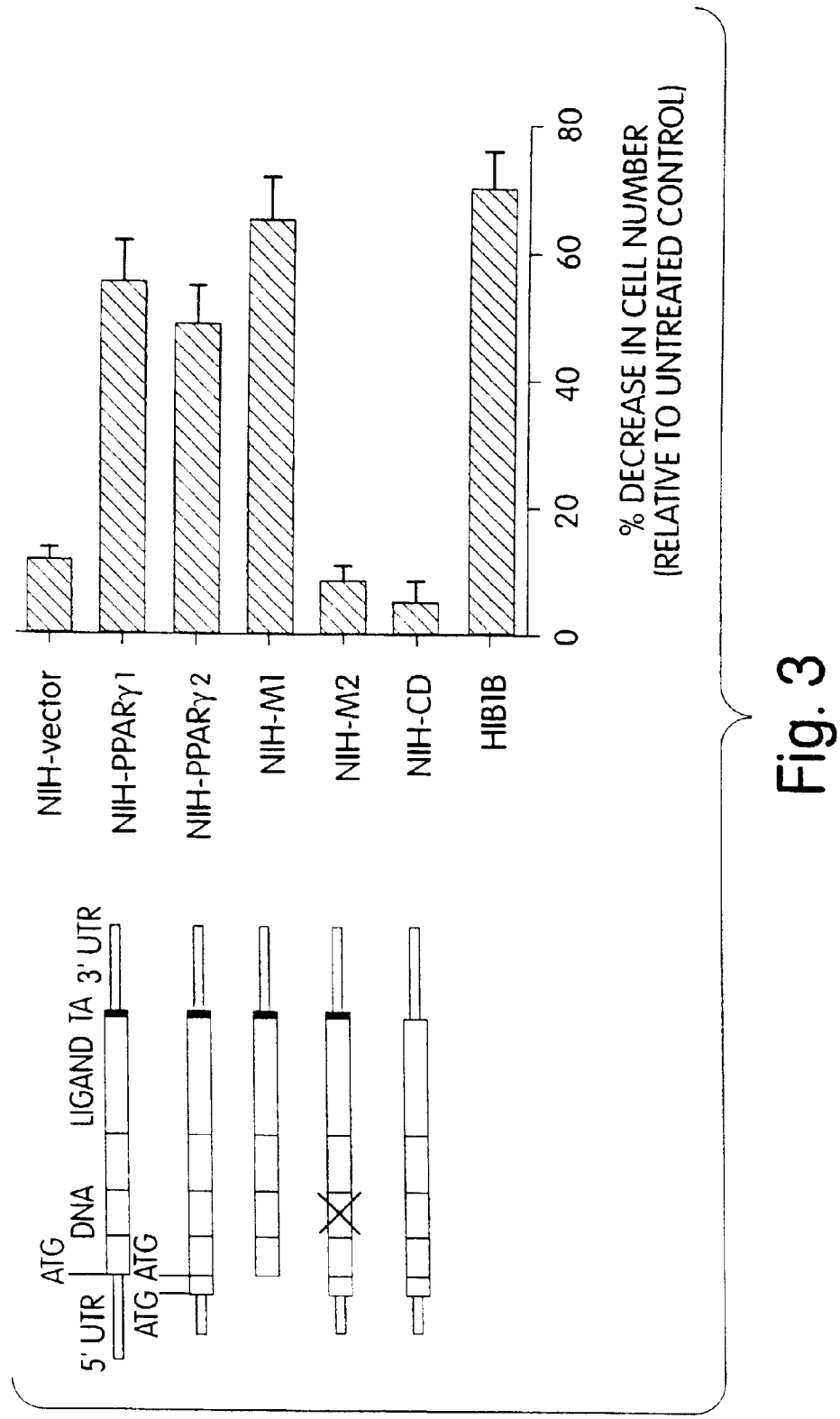

(iii) Transcription factor activity is required for PPARγ-mediated cell cycle withdrawal In order to determine some of the structural requirements of PPARγ necessary for growth arrest, NIH3T3 cells were infected with retroviral expression vectors containing wild type or various mutant forms of PPARγ cDNA. Exponentially growing cells were treated for 5 days with pioglitazone and cell numbers were determined. As shown in FIG. 3, ligand activation of both PPARγ1 and PPARγ2 induced a similar growth arrest. We also examined an allele of PPARγ (PPARγ-M1) which lacks the N-terminal 127 amino acids of PPARγ2. Previous work has shown that this allele is more active than the wild type with respect to the induction of adipogenesis (Tontonoz, P. and Spiegelman, B. M. (1994) Cell 79:1147–56). Growth inhibition in NIH3T3 cells containing PPARγ-M1 (NIH-M1) was even higher than the cells ectopically expressing wild type PPARγ1 or PPARγ2. To investigate if DNA binding and the transcriptional activation domain of PPARγ are required for its effect on cell growth, NIH3T3 cells were infected with two mutant forms of PPARγ: PPARγ-M2, containing two point mutations in the DNA binding domain and a carboxy-end deleted PPARγ-CD, which lacks the activation domain (AF-2) located in the carboxyl terminal region of all nuclear receptors (reviewed by Mangelsdorf and Evans, 1995). NIH-M2 cells express a PPARγ2 receptor in which cysteine residues at the DNA binding domain at positions 156 and 159 have been changed to serine; NIH-CD cells express a truncated form of PPARγ2 which lacks the conserved carboxyl terminal transactivation domain. Thus, pioglitazone treatment did not have any affect on cell growth and adipogenesis in NIH-M2 and NIH-CD cells. Treatment with pioglitazone caused about a 10% decrease in cell growth in NIH-vector cells. Cell numbers were determined after 5 days treatment without or with 5 μM pioglitazone. Decrease in the cell number in treated plates was represented as relative change to untreated control plates. The data represent the average of at least three independent experiments. These results demonstrate that both PPARγ1 and 2 can stimulate cell cycle withdrawal. These data also suggest that the activity of PPARγ as a DNA binding protein and transcription factor is required for its effect on cell growth.

(iv) Ligand activation of PPARγ induces growth arrest in transformed cells

We showed that PPARγ activation leads to cell cycle withdrawal of normal fibroblastic cells ectopically expressing PPARγ. To test if activation of PPARγ has the same effect on transformed cells, we used HIB1B cells, transformed with the SV40 large T antigen (SV40LT), as a model system. HIB1B cells, expressing high amounts of PPARγ1, were established from brown fat tumors of transgenic mice that constitutively express SV40LT under the control of the adipocyte specific aP2 promoter (Ross, S. R. et al. (1992) PNAS USA 89:7561–5). Exponentially growing HIB1B cells were treated with pioglitazone, cell numbers were determined and BrdU incorporation experiments were performed to evaluate the effect of PPARγ activation on cell cycle progression. As shown in FIGS. 2A, 2C and FIG. 3, PPARγ activation by pioglitazone or BRL49653 strongly repressed the growth of these cells. BrdU incorporation into newly synthesized DNA was also decreased 85% after 5 days of treatment with pioglitazone (Table 1). These results show that PPARγ activation can overcome SV40LT driven transformation and cause cell cycle withdrawal in HIB1B cells.

EXAMPLE 2

Terminal Differentiation of Human Liposarcoma Cells Induced by PPARγ- and RXR-Specific Ligands (i) Experimental Procedures Tissue samples and cytogenetics Normal human tissues, liposarcomas and other soft tissue sarcomas were obtained from surgical cases at the Brigham and Women's Hospital, Boston. All tissue samples were taken from homogeneous and viable portions of the resected sample by the pathologist and frozen within 10 minutes of excision. Hematoxylin and eosin stained sections of each soft tissue sarcoma were reviewed by a single pathologist (C.F.) and classified according to histologic type, grade, mitotic activity and surgical margin. Histologic classification was based solely on morphologic pattern recognition using conventional diagnostic criteria (Enzinger 95, Fletcher CDM 95 1043–1096). Mitotic activity counts were performed with high power field size of 0.120 mm² and at least 50 high power fields were counted from the most cellular areas of the tumor. For cytogenetic analysis tumors were dissagregated with collagenase and harvested after 3–7 days of culture in T25 flasks (Fletcher et al, 1990, Cancer Res). Metaphase cell harvesting and slide making methods were described previously (CR). Metaphase cells were analyzed by trypsin-Giemsa (Seabright (1971) *Lancet*) and quinacrine mustard banding (Fletcher (1991) *Am J Path*).

Northern analysis

Total RNA was prepared from tumors and normal human tissues by guanidium isothiocyanate extraction and CsCl centrifugation (Chirgwin, J. M. et al. (1979) *Biochemistiy* 18:5294–5299). RNA was electrophoresed through formaldehyde-agarose gels, blotted to BioTrans nylon membranes (ICN) and hybridized as directed by the manufacturer. cDNA probes were labeled with [α-$^{32}$P]-dCTP by the random priming method to a specific activity of at least $10^9$ cpm/μg.

Cell culture

Primary liposarcoma cells were isolated from selected freshly harvested tumors as described previously (Fletcher, J. A. et al. (1991) *NEJM* 324:436–443) and references therein. Primary cells were plated at a density of at least $2\times10^5$ cells/ml and cultured in 60 mm dishes in RPMI containing 15% Cosmic Calf Serum (Hyclone) and 5 μ/ml insulin. Pioglitazone (Upjohn), troglitazone (Warner-Lambert), BRL49653 (BIOMOL) and LG268 (Ligand Pharmaceuticals) were dissolved in DMSO and applied to cells in a volume of less than 5 μl. The NIH-PPARγ and NIH-vector cells were derived by retroviral infection as described (Tontonoz, P. et al., (1994) supra). Differentiated cells were stained for neutral lipid with Oil Red-O (Green, H. and Kehinde, O. (1974) *Cell* 1:113–116). BrdU labeling was performed using the labeling kit (Boehringer Mannheim) according to the manufacturers instructions.

Transfection assays

The GAL4-PPARγ expression vector was constructed by PPARγ. CV-1 cells were cultured in DMEM containing 10% resin-charcoal-stripped calf serum. Transfections were performed in phenol-red free DMEM containing 10% resin-charcoal-stripped fetal calf serum by the lipofection method using DOTAP (Boehringer Mannheim) according to the manufacturer's instructions. After 2 hours, liposomes were removed and cells were cultured for an additional 40 hours in the presence or absence of thiazolidinediones as indicated. Luciferase and β-galactosidase assays were carried out as described previously (Forman, B. M. et al., (1995) *Cell* 83:803–812).

(ii) Distribution of PPARγ mRNA in Human Tissues

Figure 4:
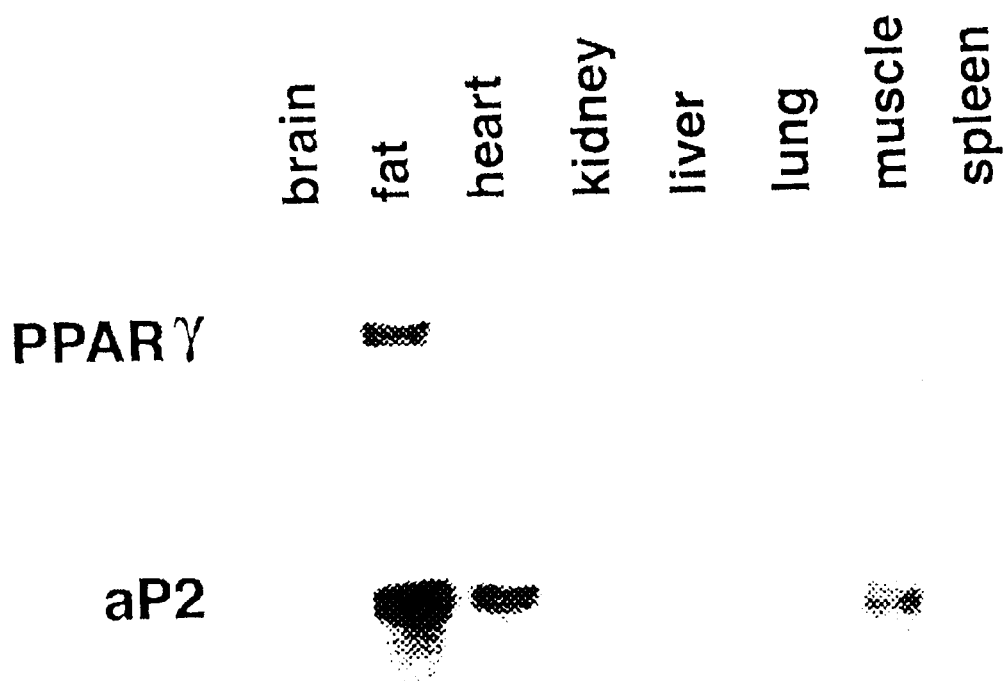

PPARγ is expressed at high levels in the adipose tissues of mouse and rat (Tontonoz, P. et al. (1994) *Nucleic Acids Res.* 22:5628–5634; Braissant, O. et al., (1996) supra). To determine the tissue distribution of this receptor in humans, we performed Northern analysis of RNA prepared from a variety of human tissues. As shown in FIG. 4, human PPARγ is expressed at highest levels in adipose tissue, and at much lower levels in several other tissues including lung and kidney. To determine whether any of the other tissue samples also contained adipose cells, the blot was also hybridized with cDNA for the adipocyte-specific binding protein aP2. The heart and muscle samples can be seen to contain significant amounts of aP2 mRNA, suggesting that at least some of the low level of PPARγ expression in these tissues results from the presence of small numbers of adipose cells.

(iii) Expression of in PPARγ Human Liposarcomas

Figure 5A:
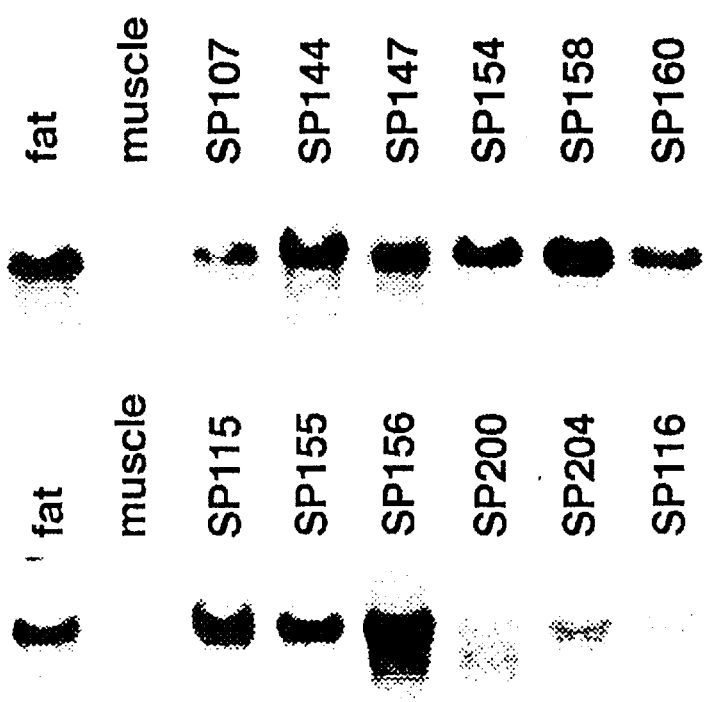
Figure 5B:
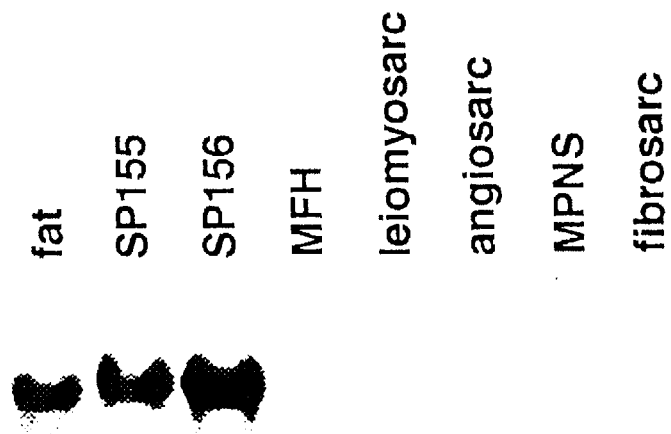

Tumorigenesis frequently involves inactivation or downregulation of genes responsible for initiating and maintaining a differentiated phenotype. As PPARγ appears to play a central role in the adipocyte differentiation process, we examined the expression of PPARγ in a series of human liposarcomas. This series included RNA prepared from each of the three major histologic subtypes of liposarcoma: well differentiated/dedifferentiated, myxoid/round cell and pleomorphic. The histologic and cytogenetic characteristics of each tumor is given in table 2. For the most part, the well differentiated/dedifferentiated tumors exhibited ring chromosomes and giant marker chromosomes, the myxoid/round cell liposarcomas exhibited the characteristic t(12;16) (Q13p11) translocation, and the pleomorphic forms exhibited complex rearrangements. Surprisingly, despite their block in differentiation, each liposarcoma examined was found to express levels of PPARγ RNA comparable to that of normal fat (FIG. 5A). These results suggest that most if not all liposarcomas have been transformed at a point in the differentiation process after induction of PPARγ expression. In contrast, PPARγ RNA was not expressed at significant levels in any other type of soft tissue sarcoma examined including leiomyosarcoma, fibrosarcoma, angiosarcoma, malignant peripheral nerve sheath tumor (MPNS), or malignant fibrous histiocytoma (MFH) (FIG. 5B). Thus, PPARγ appears to be a sensitive marker for distinguishing liposarcoma from other histologic types of soft tissue sarcoma.

Table 2: Classification of a variety of liposarcoma tumors based on their histology, cytogenetic profile, mitotic index, and primary cell cultures.

| Tumor | Histology | Cytogenetics | mitotic index | cell culture |
|---|---|---|---|---|
| 107SP | well differentiated liposarcoma | 45XX, + giant markers | 0.2 | NA |
| 115SP | high grade myxoid/round cell liposarcoma | (complex) 80–91XXXX <4N> (12;16) (Q13p11) | 6.0 | NA |
| 200SP | high grace liposarcoma, mixed pleomorphic and round cell | ND | 7.2 | NA |
| 201SP | high grade liposarcoma with pleomorphic, myxoid, well differentiated areas | ND | 19.8 | NA |
| 203SP | well differentiated liposarcoma | 48–50XY, dell6(Q23) +2–4 rings | ND | LS175 |
| 204SP | well differentiated liposarcoma | 48XX, add(7), (Q36) dell(11) (p13) +2 markers | ND | LS857 |
| P144 | well differentiated liposarcoma | 48XX, +2 rings | 0 | NA |
| P147 | well differentiated liposarcoma lipoma-like, selerosing | 46XX, add(9) (Q34) + rings, + giant markers | 0 | NA |
| P154 | atypical lipoma/well differentiated liposarcoma | ND | 0 | NA |
| P155 | intermediate grade liposarcoma myxoid>round cell component | 46XY, t(12;16) (Q13p11) | 1.0 | LS707 |
| P156 | intermediate grade liposarcoma round cell> myxoid component | 49XY, +del(1) (p3) +2, +8 t(12;16) (Q13p11) | 1.0 | NA |
| P158 | well differentiated liposarcoma | ND | 0 | NA |
| P160 | well differentiated liposarcoma with dedifferentiated areas | 43–55XX, add(1) (Q43) −11, −13, −13, +1–3 rings | 1.1 | NA |

Figure 6:
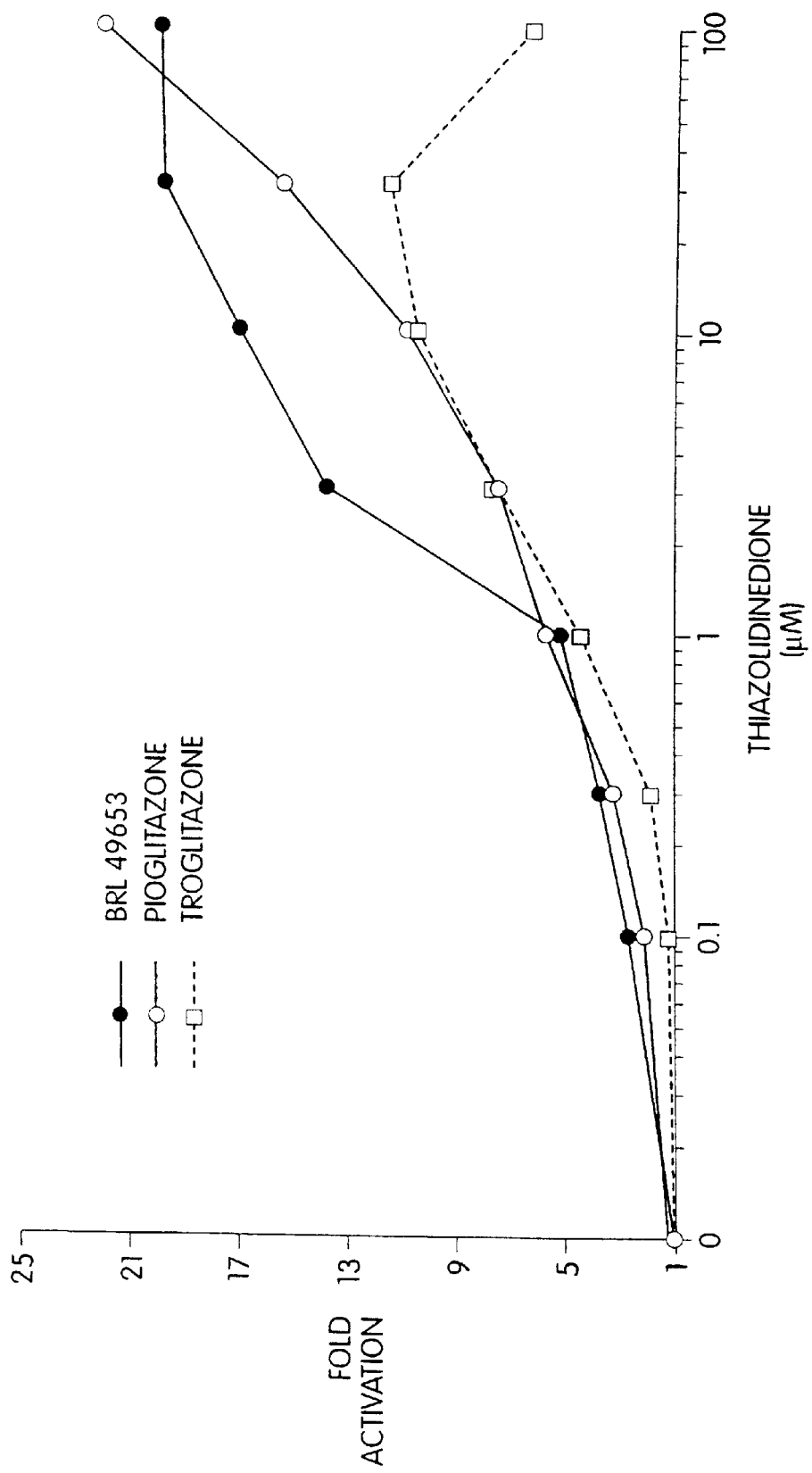
Figure 7A:
Figure 7B:
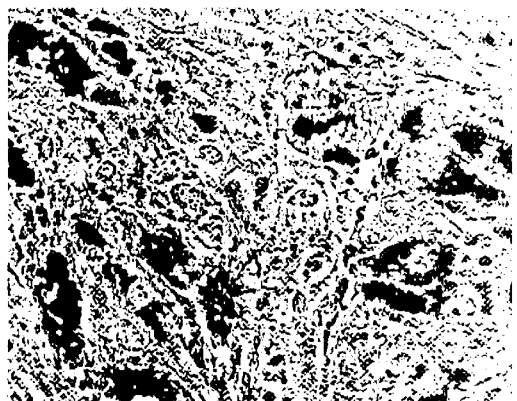
Figure 7C:
Figure 7D:
Figure 7E:
Figure 7F:
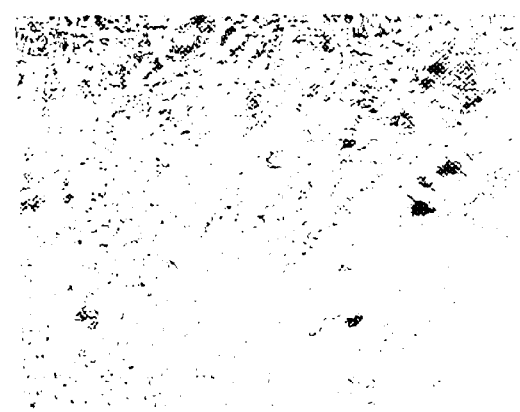

(iv) Differentiation of Human Liposarcoma Cells Induced by PPARγ- and RXR-Specific Ligands Transient transfection experiments were performed to characterize the activation profile of human PPARγ. To eliminate interference from endogenous receptor in the transfected cells, a chimeric hPPARγ receptor was utilized that could activate transcription through a heterologous response element (Forman, B. M. et al., (1995) supra). A fusion protein expression vector was constructed that contains the yeast GAL4 DNA binding domain linked to the ligand binding domain of hPPARγ. This construct was then cotransfected into CV-1 cells with a reporter plasmid containing the GAL4 upstream activating sequence. The thiazolidinedione antidiabetic drugs have recently been identified as ligand activators of the murine homologue of PPARγ. As shown in FIG. 6, the thiazolidinediones BRL49653, troglitazone and pioglitazone are effective activators of human PPARγ, and their relative potency parallels their potency as insulin-sensitizing agents in vivo (BRL>troglitazone>pioglitazone).

Liposarcomas have presumably acquired one or more genetic defects that interferes with the course of normal adipocyte development (Crozat, A. et al., (1993) *Nature* 363:640–644; Fletcher, J. A. et al., (1991) supra). The observation that PPARγ is expressed consistently in these tumors raised the possibility that the malignant cells might be forced to complete the differentiation program by maximally activating the PPARγ pathway. To address this possibility, primary cells isolated from three human liposarcomas were cultured in vitro (see Materials and Methods). Primary cell strains LS857 and LS175 were derived from well differentiated tumors and LS707 was derived from a myxoid tumor (see table 2). High-grade pleomorphic liposarcoma cells could not be expanded to sufficient numbers to permit studies of differentiation. A primary leiomyosarcoma cell line LM203 was cultured as a control. To confirm that these cultures consisted of malignant tumor-derived cells, cytogenetic analysis was performed. As shown in table 2, the karyotype of the cells in each culture was characteristic of the parent liposarcoma. Well-differentiated liposarcomas frequently contain ring chromosomes and giant marker chromosomes, whereas myxoid liposarcomas are characterized by the t(12:16) translocation (Fletcher, J. A. et al., (1991) supra).

When cultured in the presence of fetal bovine serum and insulin, conditions permissive for adipocyte differentiation, all three cell lines maintain a fibroblastic morphology. LS 175 cells contained small amounts of stainable lipid under these conditions. When cultures were treated for 7 days with 10 μM of the PPAR ligand pioglitazone, the cells readily accumulated lipid and adopted a morphology characteristic of mature cultured adipocytes (FIG. 7). No lipid accumulation was observed with the LM203 lieomyosarcoma cells which do not express PPARγ (not shown). The degree of morphologically recognizable differentiation varied from 40% in the LS 857 cells to 75% in the LS175 cells. After induction for 7 days with thiazolidinedione, cells maintained their differentiated morphology even when pioglitazone was withdrawn. This experiment was performed at least twice with each cell strain with quantitatively and qualitatively similar results. Induction of differentiation was also observed with the thiazolidinediones BRL49653 and troglitazone, while no effect was observed with compound 66, the inactive synthetic precursor to BRL49653.

Figure 8:
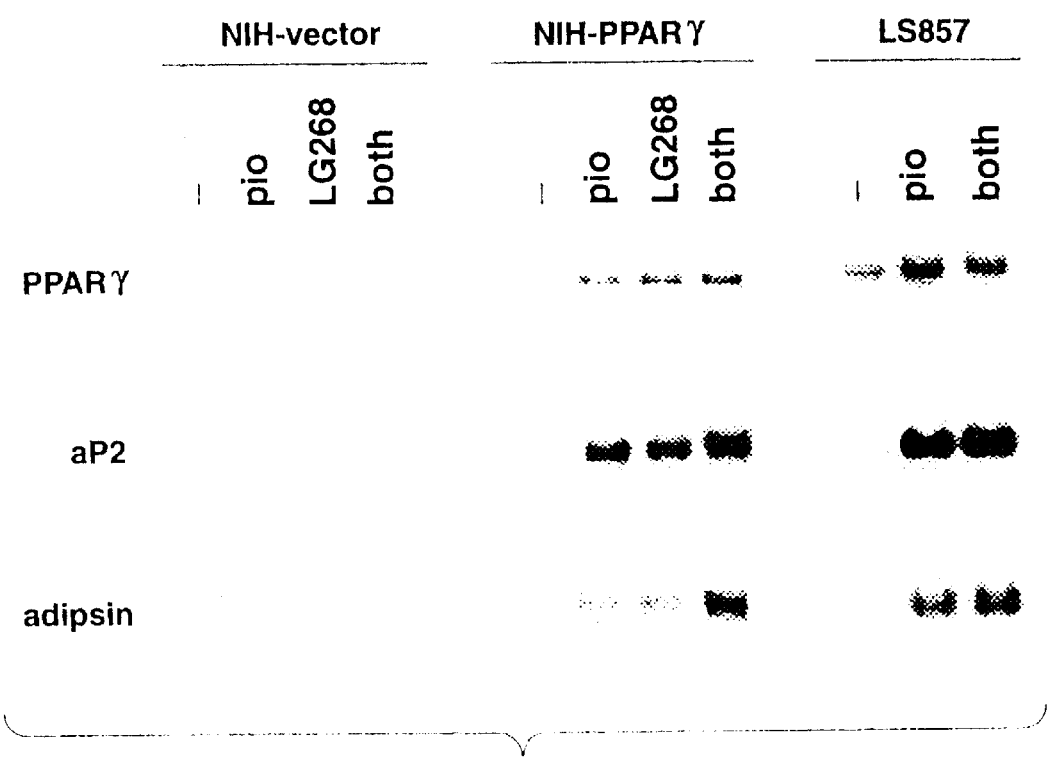

Previous work has suggested that maximal transcriptional activity of the PPAR/RXR heterodimer is achieved when both receptors are bound by their respective ligands (Kliewer, S. A. et al. (1992) *Nature* 358:771–774; Tontonoz, P. et al. (1994) supra). We hypothesized that simultaneous exposure of competent cells to both PPARγ and RXR-specific ligands might provide a stronger adipogenic signal than a PPARγ ligand alone. The ability of the RXR-specific ligand LG268 to promote adipocyte differentiation was investigated using NIH-3T3 fibroblasts that express PPARγ from a retroviral vector (Tontonoz, P. et al. (1994) supra). We have previously shown that wild-type NIH-3T3 cells express RXRAt but not PPARγ. As shown in table 3, treatment of confluent NIH-PPARγ cells for 7 days with 50 nM LG268 resulted in significant stimulation of adipocyte differentiation, comparable to that seen with 7 days of treatment with 1 μM pioglitazone alone. Simultaneous exposure to both activators resulted in an additive effect. LG268 had no effect on NIH-vector cells, indicating that the adipogenic activity of this compound, like that of pioglitazone, is dependent on the presence of PPARγ. Similar results were obtained with the preadipocyte cell lines 3T3-L1 and 3T3-F442A which express both PPARγ and RXRα (data not shown). Northern analysis confirmed that pioglitazone and LG268 had an additive effect on the induction of the adipocyte-specific genes aP2 and adipsin in NIH-PPARγ cells (FIG. 8). No induction of adipocyte gene expression was observed in NIH-vector cells under similar conditions. Table 3: Changes in adipocytic differentiation in untransfected NIH cells (NIH-vector) or NIH cells that express PPARγ from a retroviral vector (NIH-PPARγ) cultured in the absence or the presence of pioglitazone alone, LG268 alone, or in combination. Extent of adipocytic differentiation is indicated as the percentage of lipid-containing cells.

percent lipid-containing cells

| cell line | no activator | +pioglitazone | +LG268 | +pioglitazone + LG268 |
|---|---|---|---|---|
| NIH-vector | 0 | 0 | 0 | <1 |
| NIH-PPARγ | 2–5 | 60–70 | 50–65 | >90 |

Figure 9:
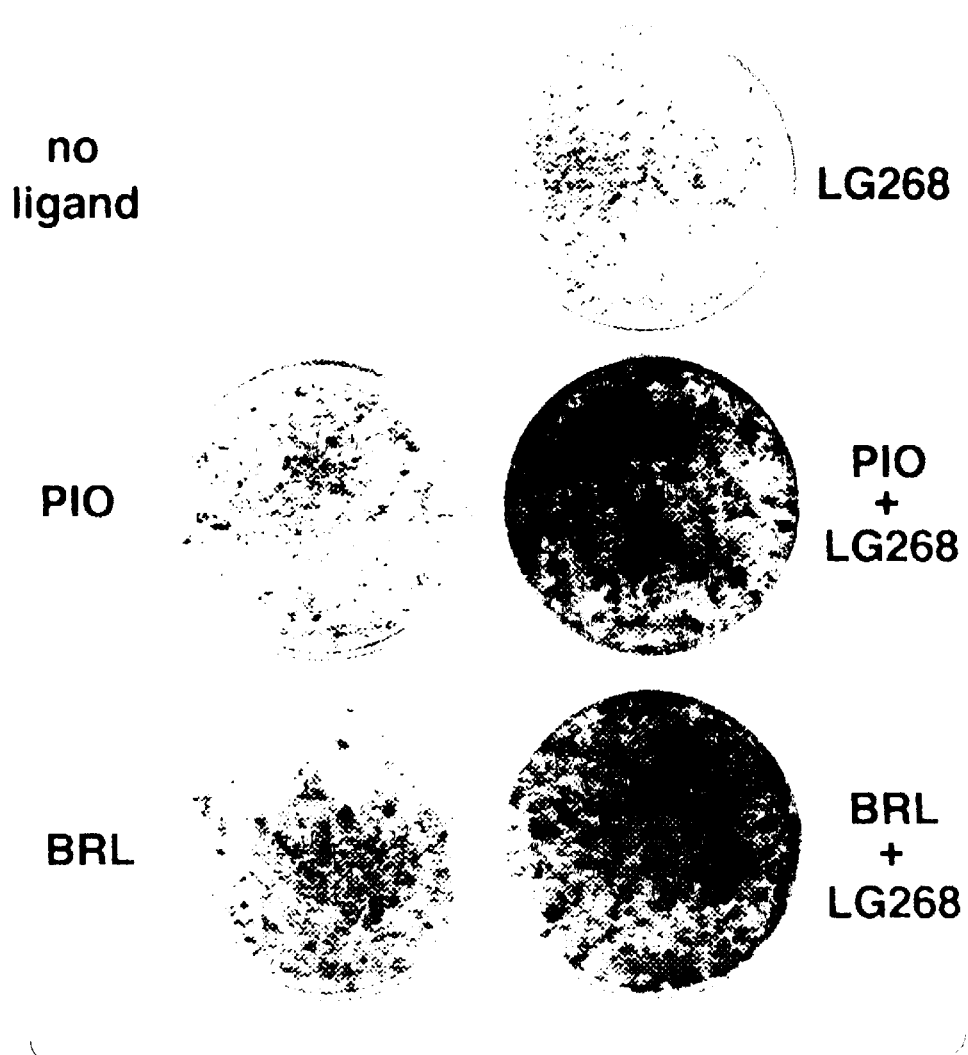
FIG. 9 is a photograph showing the morphological effects of treatment of RXR-or PPARγ-specific ligands on primary cultures of human liposarcoma cells (LS 857) with the indicated ligands: LG 268, pioglitazone (pio), both ligands (pio and LG 268), BRL 49653 alone (BRL), or in combination with LG 268 (BRL and LG 268).

We next examined the ability of LG268 to promote differentiation of human liposarcoma cells. As shown in FIG. 9, treatment of LS857 cells with 50 nM LG268 led to a significant degree of adipocyte differentiation, similar to that seen with 10 μM pioglitazone alone. When LS857 cells were treated simultaneously with LG268 and a thiazolidinedione (either pioglitazone or BRL49653) an additive effect on differentiation was observed. To further characterize the effects of PPARγ and RXR ligands on liposarcoma cells we examined the expression of adipocyte-specific markers by Northern blotting (FIG. 8). LS857 cells, like the tumor from which they were derived, express PPARγ mRNA (c.f. FIG. 5A, tumor 204SP). Treatment of LS857 cells with pioglitazone leads to the induction of two markers of terminal adipocyte differentiation, the mRNAs encoding aP2 and adipsin (FIG. 8). Simultaneous treatment with pioglitazone and LG268 results in an additive induction of adipocyte gene expression. In summary, treatment of LS857 cells with thiazolidinediones and RXR-specific retinoids leads to changes in morphology and gene expression consistent with terminal adipocyte differentiation.

Terminal differentiation of white adipocytes in vitro and in vivo is characterized by permanent withdrawal from the cell cycle. A critical question is whether thiazolidinedione-induced differentiation of liposarcoma cells is accompanied by growth arrest. To address this issue, LS857 cells were cultured in the presence or absence of pioglitazone. Following induction of morphologic differentiation, pioglitazone was withdrawn. After 48 hours of continued culture in the absence of pioglitazone, cells were labeled for 48 hours with bromodeoxyuridine (BrdU). Cells undergoing DNA synthesis during the labeling period should stain positive for BrdU incorporation after fixation and incubation with an enzyme-linked monoclonal antibody (see Experimental Procedures). In the experiment shown in table 4, 35% of the cells contained visible cytoplasmic lipid. 28% the cells in this culture stained positive for BrdU incorporation by light microscopy; however, of those cells containing lipid, only 2% stain positive for BrdU. When differentiated cultures were trypsinized and replated, lipid-containing cells failed to reenter the cell cycle as determined by BrdU labeling (data not shown). These results demonstrate that thiazolidinedione-induced differentiation of LS857 cells leads to permanent cell-cycle withdrawal.

Table 4: Effects of pioglitazone in inducing growth arrest of primary cultures of human liposarcoma cells (LS 857) in the presence or the absence of pioglitazone. Extent of adipocytic differentiation is indicated as the percentage of lipid containing cells. Degree of proliferation is indicated by the number of cells that have incorporated BrdU.

| Experiment | #cells counted | #BrdU+ (%) | #lipid+ (%) | #lipid+/ BrdU+ (%) |
| --- | --- | --- | --- | --- |
| control | 500 | 232(46) | 0 | NA |
| PIO/LG#1 | 510 | 173(34) | 204(40) | 22(4) |
| PIO/LG#2 | 595 | 156(26) | 233(51) | 17(3) |

EXAMPLE 3

Administration of Thiazolidinedione is Effective in Reducing the Size of Adipose Cell Tumors in vivo (i) Experimental Procedures Nude Mice Studies HIB1B cells ($2 \times 10^6$ cells/animal) were injected subcutaneously to the upper back of twenty four male nude mice (7 weeks NCR w/w). Thirteen days after injection, mice were treated with troglitazone (0.2% mixture with powder food). The development of tumor volume (measured in mm$^3$) was determined at days 14, 19 and 26 after troglitazone treatment compared to untreated controls. Each point represents the mean ±standard duration (SD) from 12 mice (except the last point, where n=11) treated or untreated with troglitazone for the indicated time intervals.

Sample Size Calculations

To evaluate changes in tumor size, mean (SD) from 11–12 cases for each group of animal were examined to ensure an 85% chance of detecting a statistically significant difference (assuming a 2-sided sample t-test).

Figure 10:
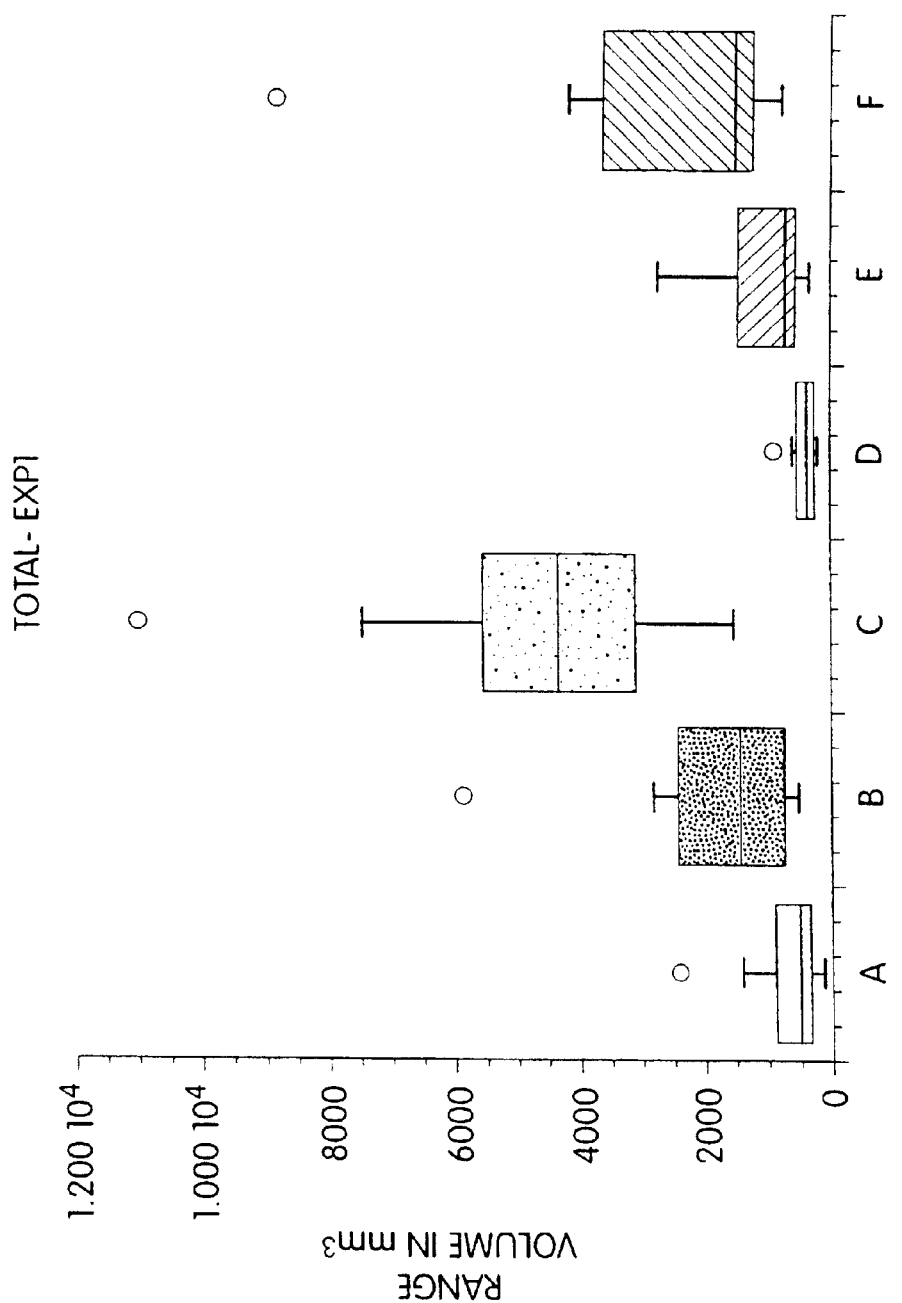
FIG. 10 is a graph depicting the effects of administration of the thiazolidinedione troglitazone on reducing the size of adipose cell tumors in nude mice.

As demonstrated by FIG. 10 and Table 5, administration of the thiazolidinedione troglitazone is effective in reducing the size of adipose tumors in nude mice. These tumors had been experimentally induced by implanting the SV40 large T-antigen transformed HIB1B cells into nude mice. FIG. 10 shows that the evolution of adipose tumors in implanted nude mice untreated and treated with troglitazone for 14, 19 and 26 days. Points A–C and D–F represent untreated and troglitazone-treated animals, respectively. Each point represents the mean ± standard deviation from 12 mice (except the last point, where n=11) Statistically significant decreases in tumor volume were detected in implanted mice treated with troglitazone compared to untreated controls. Table 1 summarizes the mean (SD) of tumor volume (measured in mm$^3$) in treated mice (Group 2) compared to untreated controls (Group 1). The tumor volume was determined after 14, 19 and 26 days of treatment. Volumes are indicated with and without outlier points in each group of animals. A comparison of the tumor volume by two-sided 2-sample t-test after 26 days of treatment indicates p=0.0019 (without outlier); p=0.037 (with outlier). To evaluate the tumor increase over time, repeated measures analysis of variance were determined, p=0.0014 without outlier; p=0.044 with outlier.

Table 5 Tumor volume (mean (SD)) in nude mice previously implanted with HIB1B cells, troglitazone-treated (Group 2) compared to untreated controls (Group 1). Mean (sd)

|  | 14 days | 19 days | 26 days |
| --- | --- | --- | --- |
| Group 1, w/o outlier | 564(349) | 1400(715) | 4195(1623) |
| Group 2, w/o outlier | 361(110) | 830(389) | 2032(1179) |
| Group 1, w outlier | 719(631) | 1774(1462) | 4763(2504) |
| Group 2, w outlier | 403(182) | 990(665) | 2601(2270) |

EXAMPLE 4

PPARγ is Expressed in Various Human Cancer Cell Lines

Figure 11:
FIG. 11 represents a Northern blot demonstrating the expression of PPARγ sub-types in various human cancer cell lines.
Figure 11:
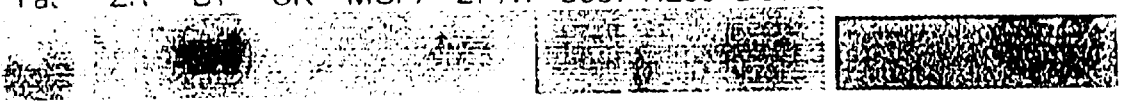

FIG. 11 represents a northern blot demonstrating the expression of PPARγ sub-types in various human cancer cell lines. The nothern blot was performed with total RNA from various cell lines as indicated. RNA loading is unequal and not comparable.

EXAMPLE 5

PPARγ agonists Inhibit Proliferation of Leukemic Cells

Figure 12:
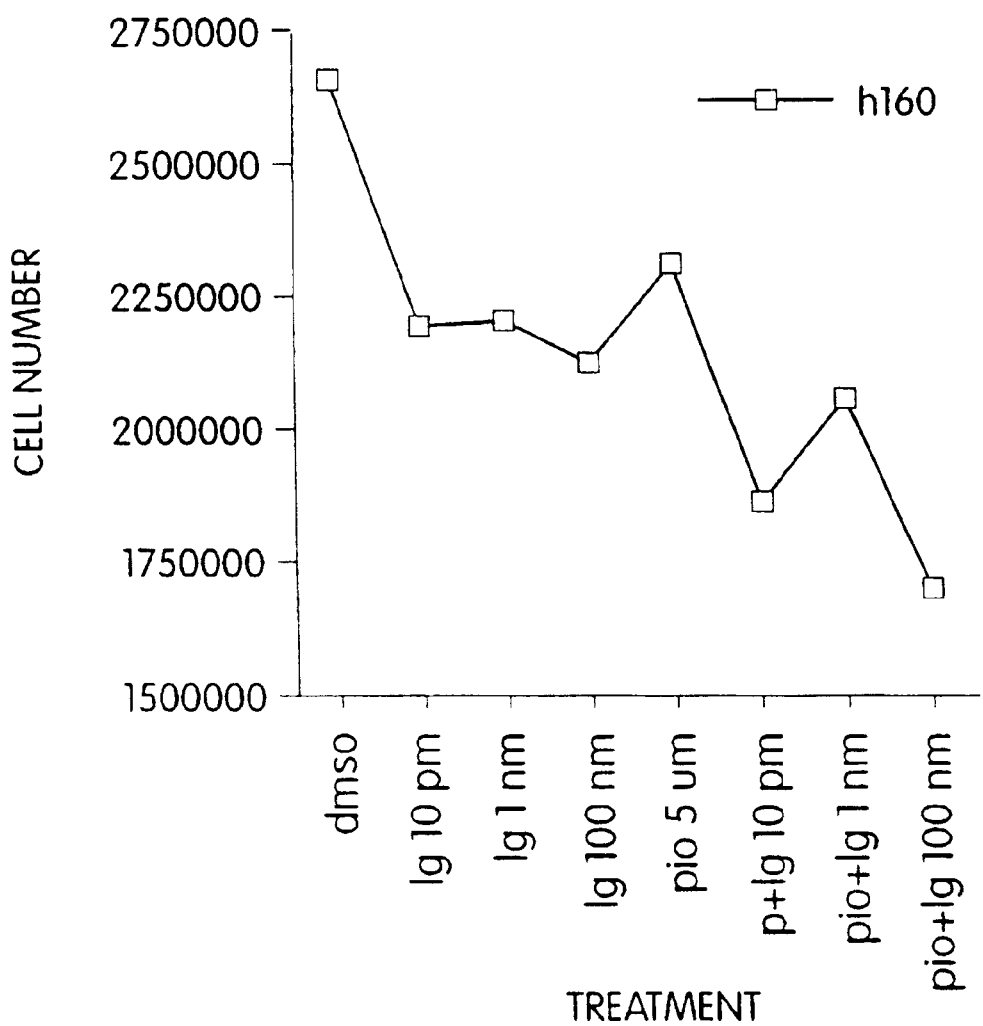
FIGS. 12 and 13 are graphs depicting the effect of LG 268 ("1g") and pioglitazone ("pio") on the HL-60 (leukemic) cell line.

We investigated the effect of PPARγ agonists on the proliferation and differentiation of the HL-60 human myeloid leukemia cell line. FIG. 12, which shows HL-60 cell numbers after 5 days of treatment, demonstrates that PPARγ agonists can cause dose-dependent inhibition of cell proliferation. Briefly, HL-60 cells were plated at 5000 cells/well in 24 well plates and treated with varying concentrations of LG 268 and pioglitazone. After 5 days, aliquots were removed and used to measure cell number via coulter counter. The values provided in the subject graph are mean values for triplicate determinations.

Figure 13:
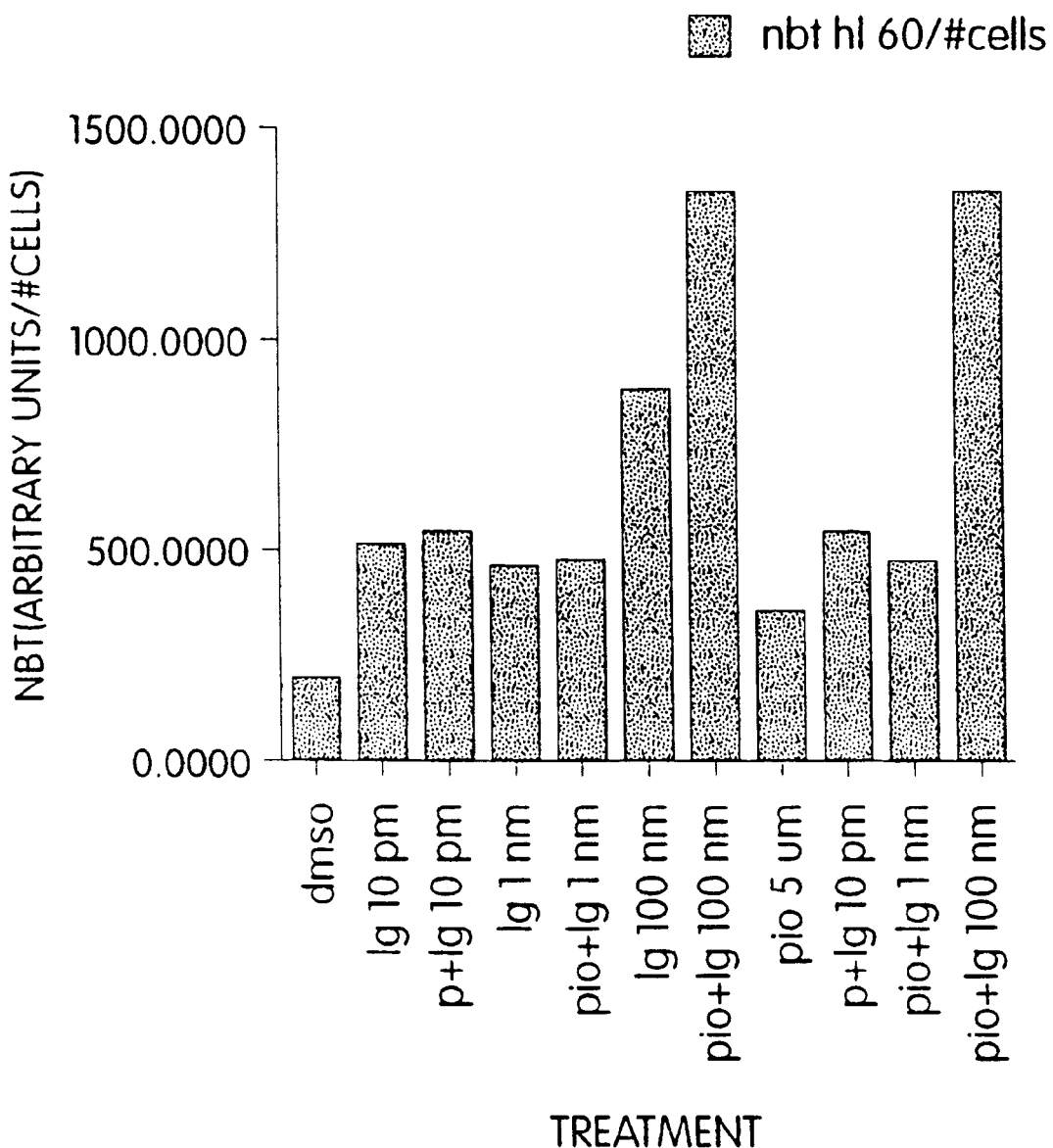

FIG. 13 demonstrates that PPARγ agonists can induce differentiation of transformed leukemic cells along a myelomonocytic pathway, as determined by nitroblue tetrazolium (NBT) reduction. Briefly, HL-60 cells in exponential growing phase were placed in 24 well plates at 5000 cells/well and treated with varying concentrations of LG 268 and pioglitazone. After 5 days, the cells were assessed for granulocytic/monocytic differentiation via the NBT assay. Higer levels of conversion of NBT correspond to greater numbers of differentiated cells in the test sample.

EXAMPLE 6

PPARγ agonists Inhibit Proliferation of Prostate Cancer Cells

Figure 14:
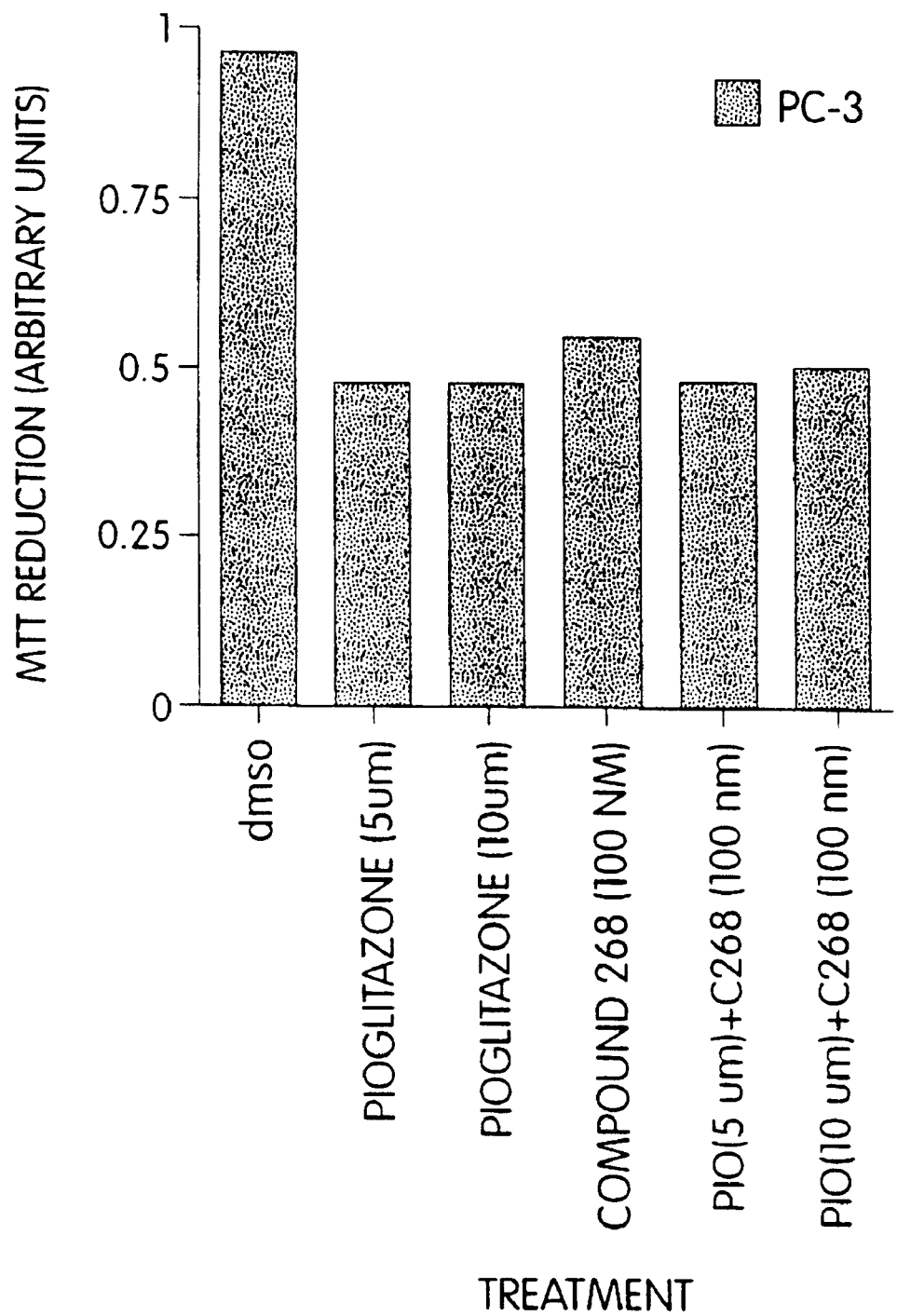
FIG. 14 is a graph depicting the effect of LG 268 ("compound 268") and pioglitazone ("pio") on the human prostrate cancer cell line PC3.

FIG. 14 is a graph depicting the effect of LG 268 ("compound 268") and pioglitazone ("pio") on the human prostrate cancer cell line PC3. Briefly, PC3 cells were plated at 2000 cells/well in 96 well plated and treated with varying concentratios of LG 268 and pioglitazone. After 5 days, viability was assed by the 3-(4,5-dimethylthiazol-2-yl)-2,5-diphenyltetrazolium-bromide (MTT) assay in order to determine the degree of drug-induced inhibition. The MTT assay is based on cleavage of tetrazolium bromide by metabolically active cells, resulting in a quantitative blue color.

EXAMPLE 7

Terminal Differentiation of Human Breast Cancer: Expression and Ligand Activation of PPARγ

(i) Experimental Procedures
Chemical reagents and cell lines

Pioglitazone was provided by Upjohn Co, Kalmazoo, Mich. Troglitazone and PD147275 (M2) were obtained from Parke-Davies/Warner-Lambert, Ann Arbor, Mich. 15-deoxy-$\Delta^{12,14}$-prostaglandin $J_2$ and PD98059 were from Cayman Chemical and New England Biolabs, respectively. LG268 was obtained from Ligand Pharmaceuticals, La Jolla Calif.
Cell culture Cell lines ZR-75-1, MCF-7, BT-20, SK-BR3 were obtained from ATCC and cultured in media suggested. 21NT, 21PT and 21MT [Band, V. et al., *Cancer Research* 50:7351–7357 (1990)] cells were grown in α-Medium [Band, V. et al., *Genes, Chromosomes & Cancer* 48–58 (1989). For differentiation assay, cells were cultured in α-MEM containing 10% cosmic calf serum (Hyclone), 2 mM L-glutamine, 2 mM sodium pyruvate, 0.1 mM nonessential amino acids, 5 μg/ml of insulin, 2.8 μM hydrocortisone, and, for 21 MT, 1 μg/ml sheep prolactin. Cells were refed every 48 hr. At 7–10 days after treatment, total RNA was isolated and cells were fixed and stained with Oil Red O [Greene, H. * Kehinde, ). *Biochemistry* 18:5294–5299 (1979) or Nile Red. For growth assay, exponentially growing cells were plated at 500 cells/well in 24 well plates. After 1 day, cells were treated with α-MEM containing 10% charcoal stripped FBS (Hyclone), 2 mM L-glutamine, 1 mM sodium pyruvate, 0.1 mM nonessential amino acids, 5 μg/ml of insulin, 1 mM dexamethasone. Cells were refed every 36–48 hr. At day 3 and 7 after treatment, $^3$H-thymidine (2 μCi/ml) was added to the cells for 18–24 hours and incorporation in DNA was detected by scintillation counting. For clonogenic assay, after 7–10 days of culture in differentiation medium in the presence of vehicle (DMSO) or 10 μM troglitazone, cells were tripsinazed, counted with triptan blue exclusion. Cells were replated in 10 cm$^2$ plates at 10$^3$ cells per plate. After 15 days, cultures were stained with crystal violet.
RNA analysis Total RNA was isolated from cultured cells and tissues by guanidine isothiocyanate extraction [Chirgwin, J. M. et al., *Biochemistry* 18:5294–5299 (1979)]. RNA was denatured in formamide and formaldehyde and electrophoresed in agarose gels containing formaldehyde as described [Maniatis, T., et al. *Molecular Cloning: A Laboratory Manual,* second edition (Cold Spring Harbor Laboratory Press, Cold Spring Harbor N.Y. (1989)]. RNA was transferred to BioTrans nylon (ICN Pharmaceuticals) and membranes were cross-linked, hybridized and washed as directed by the manufacturer. Equal loading of RNA was ensured by ethidium bromide staining and by hybridization to cDNA for human acid riosomal phosphoprotein PO (26B40 [Laborada, *J. Nucleic Acids Res.* 19:3998 (1991)] and actin cDNA probes were labeled with α-$^{32P}$dCTP (6000 Ci/mmol) by the random-priming method [Finberg A. P. & Vogelstien, B. A. et al., *Anal. Biochem* 137:266–267 (1984)] to a specific activity of at least 10$^9$ cpm/μg.
Western blot analysis Whole cell extracts from MT cells, SDS-polyacrylamide gel electrophoresis (PAGE) and protein immunoblot were performed as described [Hu, e. et al. *Science* 274:2100–2103 (1996). The antibody against PPARγ has been previously described [ibid.]. The antibody against the activated phosphorylated MAP Kinase was obtained from Promega and used as recommended. Polyclonal rabbit anti-human PPARγ antisera was raised to an affinity purified glutathion S. Transferase—full length human PPARγ fusion protein.

(ii) PPARγ expression in breast development

To investigate whether PPARγ might function in pathological breast development, we first examined expression at the mRNA level in a variety of mammary epithelial cancer cell lines. As a control, we loaded an RNA sample for adipose tissue, known to have the highest level of PPARγ mRNA (FIG. 15), while half showed significant expression, with levels varying from 10%–40% of those seen in fat. Three of these cell lines, all estrogen receptor negative, represent a series developed by the laboratory of Dr. Ruth Sager from a single patient diagnosed with infiltrating and intraductal carcinoma of the breast [Band, V. et al., *Cancer Research* 50:7351–5357 (1990)]. The 21NT and 21PT cells were derived from the primary tumor, whereas the 21MT cells were derived from a pleural effusion when this same patient relapsed with breast cancer metastatic to the lung. While both the primary and metastatic breast cell lines express PPARγ, the 21MT cells express the highest level, which amounted to 30% of that seen in fat tissue.

(iii) PPARγ expression in normal breast epithelial tissue

Determination of PPARγ expression in normal breast epithelium and from primary breast tumors may be hampered by the large amount of fat contained in the normal breast which is difficult to separate completely from the primary breast tumor. For this reason, we studied four different patients with disease that had metastasized to the lung. Surgically resected metastatic breast tumors were completely separated from the normal surrounding lung and analyzed for PPARγmRNA expression by Northern blotting. As shown in FIG. 15, each of these samples were positive, showing approximately 10% the level of PPARγmRNA seen in fat.

Figure 16A:
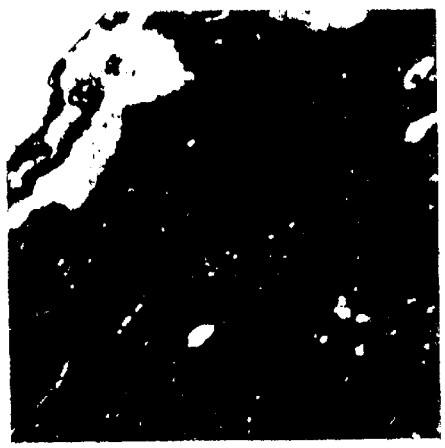
Figure 16B:
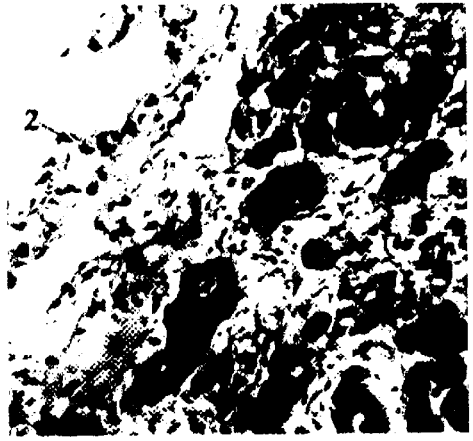
Figure 16C:
Figure 16D:

To determine the distribution of PPARγ protein in benign and malignant breast tissues we performed avidin-biotin complex immunocytochemistry using an antibody prepared against mouse PPARγ developed in our laboratory; FIG. 16a depicts the typical appearance of a metastatic infiltrating ductal adenocarcinoma to the lung in standard haematoxylin and eosin (H and E) staining. On the same histologic section stained with the PPARγ antibody (FIG. 16b) there is intense (brown) nuclear staining of the metastatic breast adenocarcinoma cells (arrow 1). There is also positive nuclear staining of lung type II pneumocytes (arrow 2) in the generally negative lung tissue. We saw a similar PPARγ staining pattern for all four metastatic human breast tissues analyzed. PPARγ immunohistochemistry of normal breast tissue demonstrated intense brown nuclear staining of the normal breast epithelial cells lining ducts (arrow 3) as well as adjacent normal fat cells (arrow 4) (FIGS. 16c–d). Preimmune sera showed no nuclear staining of breast cancer, normal breast tissue, adipocytes or lung pneumocytes (data not shown).

(iv) Activation of PPARγ

Figure 17A:
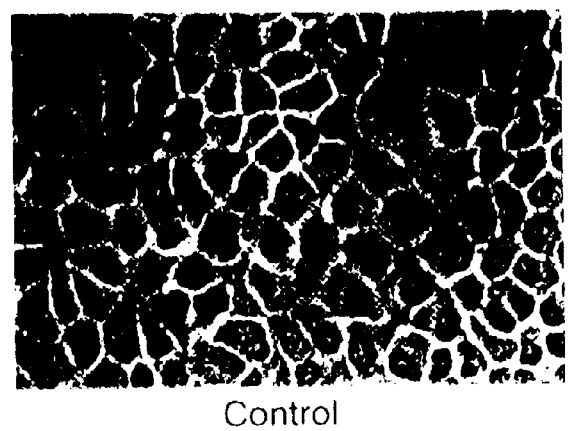
Figure 17A:
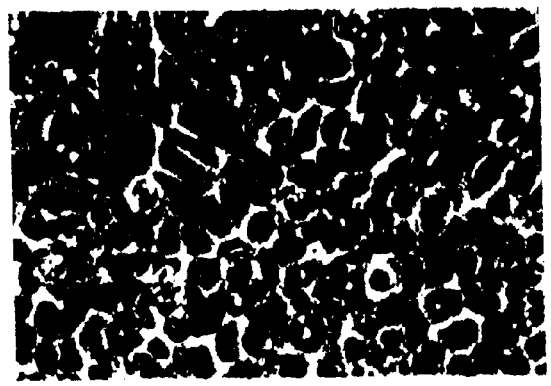
Figure 17A:
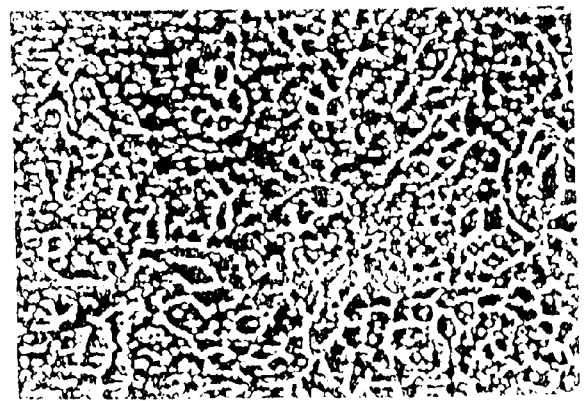

To determine the effects of activation of PPARγ in malignant breast cells, TZD ligands were applied to the 21PT and 21MT cells discussed above. When the 21PT cells were treated for 7 days with two different PPARγ ligands, pioglitazone and troglitazone, the cells underwent a morphological conversion, rounding up and filling with neutral lipid that stained with Oil Red O (FIG. 17a). In contrast to these cells, only a small degree of morphological conversion was observed with the 21MT cell line (FIG. 17c), despite the fact that it expressed higher levels of PPARγ mRNA (FIG. 15).

Figure 17B:
Figure 17B:
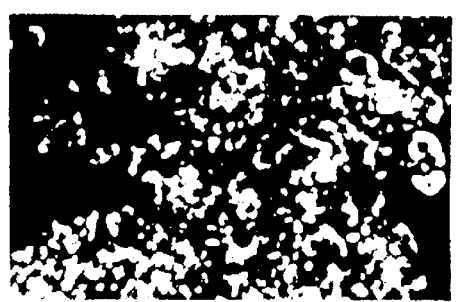
Figure 17B:
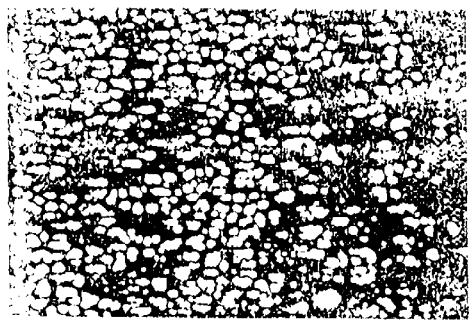
Figure 17B:
Figure 17C:
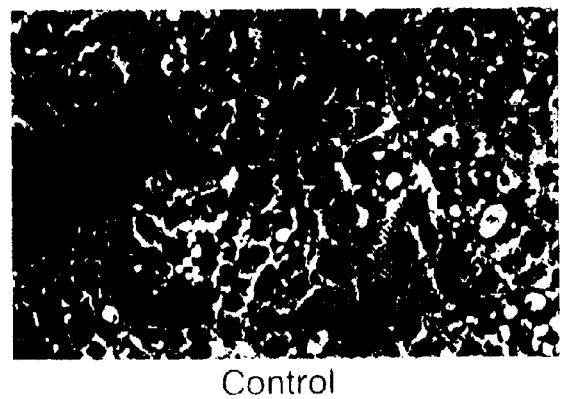
Figure 17C:
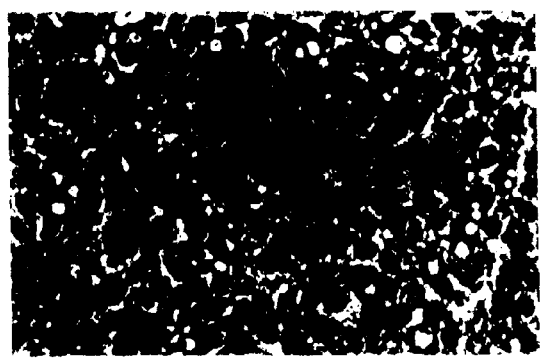
Figure 17C:
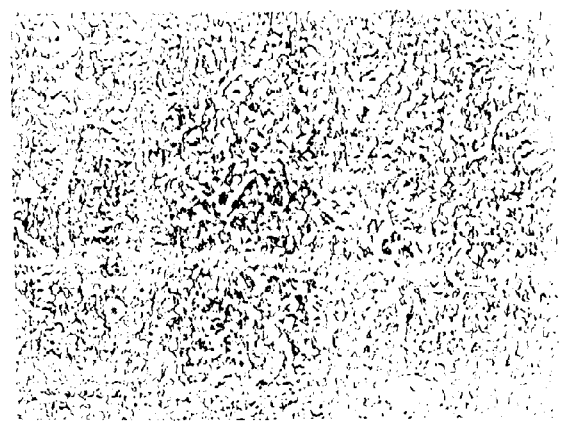

These data suggest a remarkable cellular response in some breast cancer cells to the TZDs. To confirm that this response is the result of PPARγ activation, we used another ligand for PPARγ of an entirely different chemical class, 15-deoxy-$\Delta^{12,14}$-prostaglandin $J_2$($PGJ_2$) [Kliewer, S. A. et al. *Cell* 83:813–810 (1995); Tontonoz, P. et al. *Proceedings National Academy of Sciences of the USA* 94:237–241 (1997)]. This compound also stimulates significant lipid accumulation in 21PT cells as illustrated in FIG. 3b with Nile Red staining for lipids. In contrast a metabolite of troglitazone that has no affinity for PPARγ, termed MS (A. Saltiel, pers. com), does not induce this response (FIG. 17b). Thus, activation of PPARγ can stimulate a dramatic morphological conversion and lipid accumulation in a malignant breast cell line However, at least one breast cancer cell line (21MT) expressing high levels of PPARγ illustrates a relative resistance to this consequence of receptor activation.

Figure 18A:
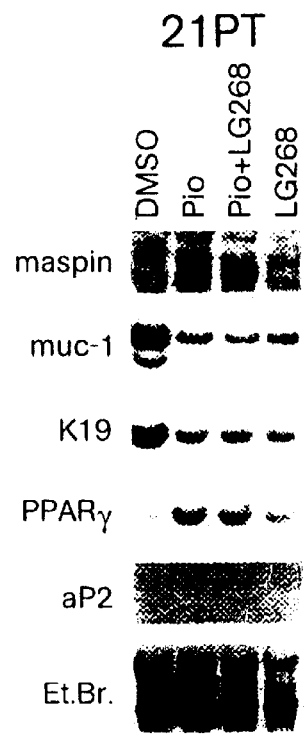

In order to characterize the effects of PPARγ activation at a molecular level, we examined patterns of gene expression in 21PT cells treated for one week with TZDs (FIG. 18a). Pioglitazone (Pio) treatment induces mRNA for PPARγ in these cells, as has been shown in fat differentiation [Brun, R. P. et al., *Genes & Development* 10:974–984 (1996)]. lg268 (LG), an RXR specific ligand also does this, but to a more limited extent. The combination of pioglitazone and LG268 at these doses is not more effective than the TZD alone. These agents do not lead to expression of adipsin (data not shown) and aP2, two well established markers of adipogenesis, indicating that these lipid laden cells are not undergoing "trans-differentiation" to adipocytes. We also examined maspin, a serine protease inhibitor that is usually expressed in normal mammary epithelium and that also has tumor suppresser activity in animal models [Zou, Z. et al. *Science* 256:526–529 (1994)]. The expression of this mRNA is almost undetectable in vehicle treated cells but is induced by pioglitazone treatment. Conversely, keratin 19 (K19) and mucin-1 (Muc-1), two genes whose expression have been used as markers of malignancy [Regimbald, L. H. et al. *Cancer Research* 56:4244–4249 (1995)], are suppressed by treatment with either pioglitazone or LG268. Some markers (Muc-1 and K19) are almost as sensitive to RXR stimulation as they are to the activation of PPARγ, but simultaneous activation of both receptors is not additive above this (presumably maximal) stimulation of PPARγ alone. These results show that activation of the PPARγ /RXR heterodimer causes changes in gene expression more characteristic of the normal, non-malignant phenotype.

Figure 18C:
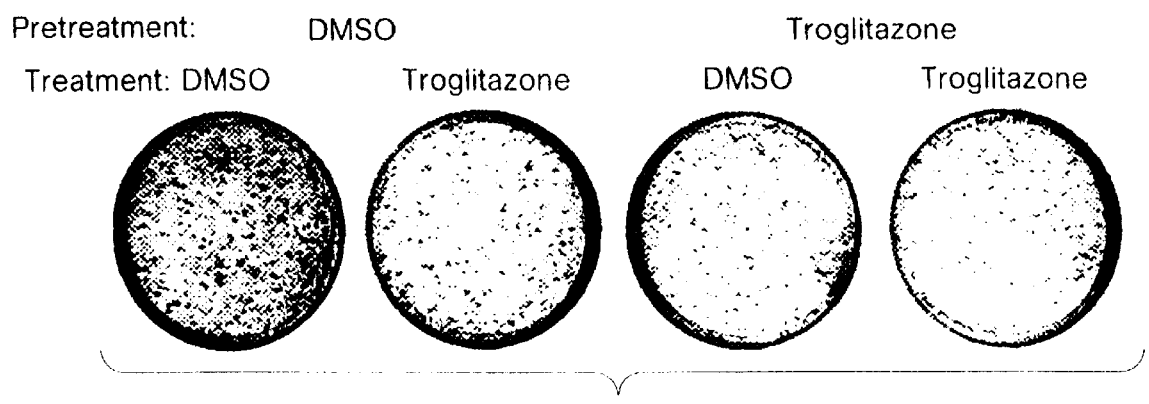
Figure 18B:
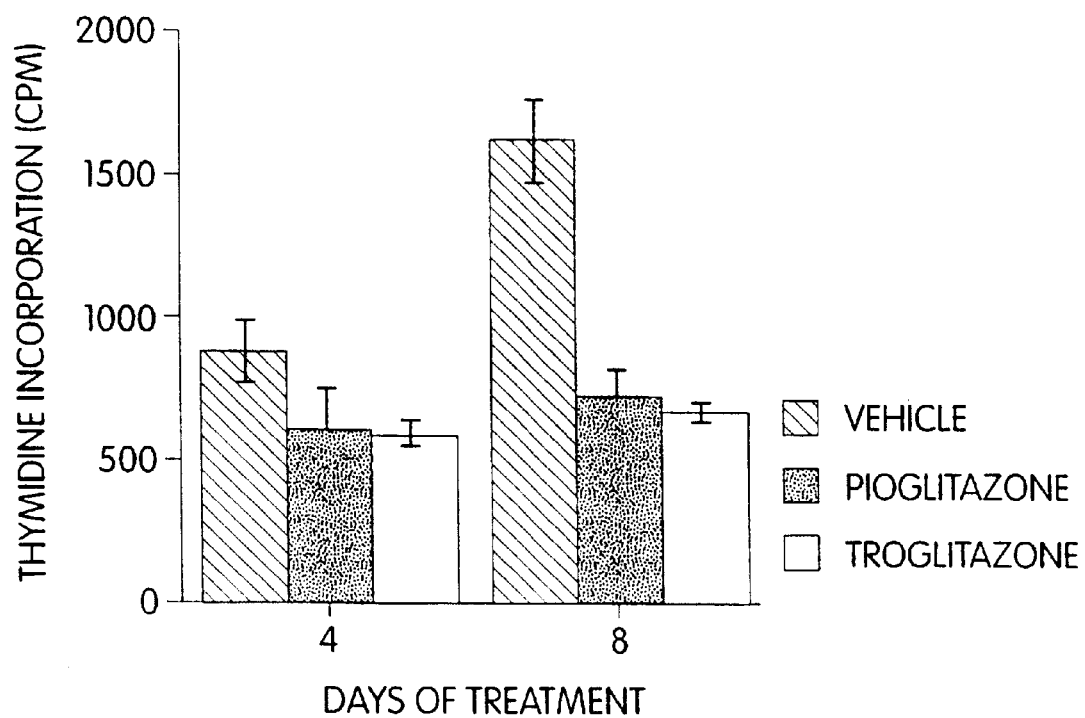

The effects of ligand activation of PPARγ on cell growth was studied first by examining thymidine incorporation in sparse, rapidly growing cultures of 21PT cells. As shown in FIG. 18b, four days of treatment with pioglitazone or troglitazone results in a 30% decrease in the incorporation of thymidine. After eight days there was a further increase in thymidine incorporation in the vehicle treated cells, reflecting a continuous cell growth. In contrast, in cultures treated with two TZD ligands, troglitazone and pioglitazone, there was essentially no further increase in thymidine incorporation, presumably due to a decreased growth rate in these cells. It is notable that this is not an acute effect, but takes several days to develop, consistent with a differentiation-type response.

(v) MAP kinase inhibitors potentiate activation of PPARγ

Growth was also investigated in a two-step clonogenic assay. These same cells were treated first for 15 days with troglitazone or vehicle (DMSO). They were then trypsinized and plated at low density into the same media or "crossed-over" to the other condition. The equivalence of cell numbers plated and cell viability was ensured by counting cells and examining their ability to exclude tryptan blue. Clonogenic growth was allowed to proceed for two weeks. As shown in FIG. 18c, the cells that were in vehicle for both pretreatment and treatment developed the most numerous, largest and densest colonies. Cells exposed to troglitazone for both pre- and subsequent treatments showed the fewest colonies, smaller in size and were also less densely staining. Interestingly while cells pretreated with control medium and then "crossed-over" into troglitazone showed some reduction in colony number and density, cells pretreated with troglitazone and then released into control medium has marked reduction in clonogenic growth, essentially equivalent with those kept continuously in ligand. These results show that activation of PPARγ reduces clonogenic cell growth, and also suggests that this effect, once developed, is not immediately reversed by ligand removal.

Figure 19A:
Figure 19A:
Figure 19A:
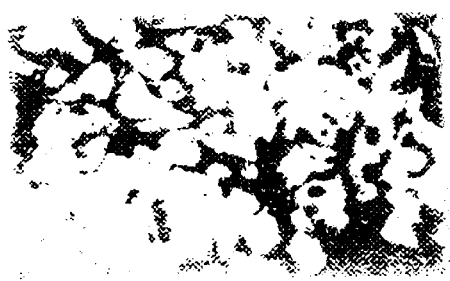
Figure 19A:
Figure 19B:
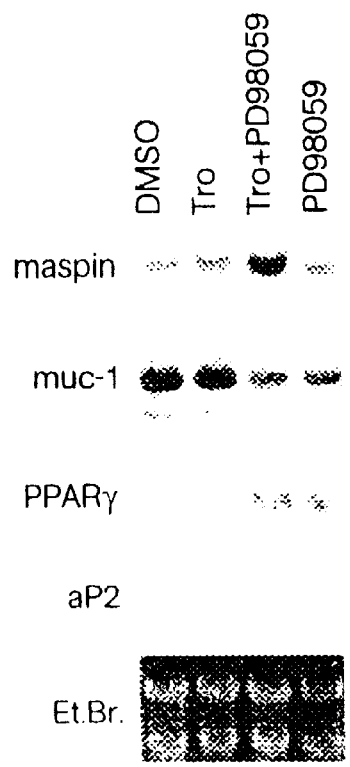
Figure 19C:
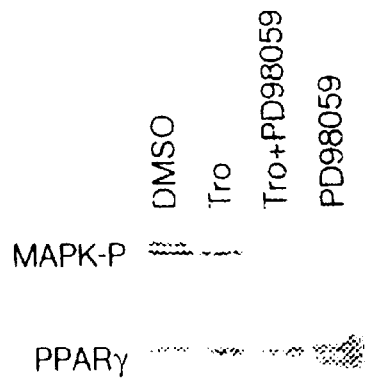

It is striking that the breast cell line that has the highest level of PPARγ expression shows minimal response to TZD activation. We [Hu, E. et al. *Science* 274:2100–2103 (1996)] and others [Adams et al., *J Biol Chem* 272:5128–5132 (1997); Camp et al., *J Biol Chem* 272:10811–10816 (1977)] have recently shown that MAP kinase can directly phosphorylate PPARγ at serine 112 and this phosphorylated form of the receptor has greatly reduced transcriptional activity and less ability to promote differentiation. We therefore asked whether a high endogenous MAP kinase activity present in 21MT cells could account for their poor response. As shown in FIG. 19a, application of PD980–59, a MAP kinase kinase (MEK) inhibitor, to these cells caused an increase in lipid accumulation, relative to vehicle-treated cells. Furthermore, while no more than 10% of cells treated with troglitazone alone stained with Oil red 0, the combination of troglitazone and PD98059 caused at least half of the cells to accumulate lipid. FIG. 19c illustrates that the PD98059 reduced the levels of activated MAP kinase in these cells. Consistent with these data, PD98059 treated cells show more of the unphosphorylated, more active form of PPARγ, which has been shown to have a faster electrophoretic mobility than the MAP kinase phosphorylated form [Hu, E. et al., *Science* 274:2100–2103 (1996)].

An impressive cooperation between troglitazone and PD98059 can also be seen at the level of gene expression. FIG. 19b shows that troglitazone is ineffective at activating maspin expression in the 21MT cells, as is PD98059. However, the combination of both agents effectively activates this marker characteristic of the normal state. Similarly, troglitazone is a much more effective suppresser of Muc-1 mRNA expression in the presence of the MEK inhibitor, strongly suggesting that MAP kinase is reducing the activity of PPAR-Y in these highly malignant cells.

The activation of PPARγ by TZDs causes a remarkable morphological and biochemical response in breast cancer cells. Neutral lipid accumulation is prominent, as are changes in gene expression. This includes increased expression of a marker of normal breast development, the protease inhibitor maspin, that has been shown to have tumor suppresser activity in ectopic expression/transplantation studies (Zou, Z. et al. *Science* 256:526–529 (1994)]. Conversely, two epithelial markers associated with a malignant state, mucin-1 and karatin 19, are both suppressed by PPARγ activation. While the cells appear morphologically similar to cultured fat cells, they express no markers characteristic of this lineage. Hence, these cells can best be described as undergoing fatty epithelial differentiation, perhaps recapitulating some version of a lactation response. This response does not appear to be specific for cancer cells. HC11, a murine cell line established from normal tissue, shows a similar lipid accumulation and changes in gene expression with TZD activation of PPARγ (data not shown).

It is also noteworthy that maspin and Muc-1 may have significant roles in malignancy itself. Maspin is a serine protease inhibitor which was first identified in mammary tissue and proposed to be a tumor suppresser gene based on a number of in vitro and in vivo observations (Zou, Z. et al, *Science* 256:526–529 (1994)]. Its expression pattern is high in normal breast tissue and breast-derived cells while various tumor cell lines show low or zero expression. Functional studies have demonstrated that maspin expression inhibits the motility of human mammary tumor cells in culture, as well as the growth and metastasis of tumors in nude mice. Muc 1 is a cell associated mucin glycoprotein that is usually expressed on the apical borders of secretory mammary epithelial cells. It is aberrantly expressed at very high levels in metastatic breast cancers [Kufe, D. et al. *Hybridoma* 3:223–232 (1984)]. Although the precise function of Muc 1 is not known, its high expression in carcinomas reduces cell to cell and cell to extracellular matrix contact, possibly due to its large size and high negative charge. A direct role for Muc-1 in tumor progression has been demonstrated in Muc1-/-mice, where tumors induced by polyoma middle T antigen in breast tissue were found to have a significantly slower growth rate in Muc 1 deficient mice compared to control mice [Spicer, A. P. et al., *J B C* 270:30093–30101 (1995)].

Activation of PPARγ causes a slowing or cessation of cell growth in the breast cancer cells studied here. This is not a sudden, cytotoxic response, but appears to be more a differentiative response, occurring over several days, as does the lipid accumulation. One potentially important finding is that once TZD activation of PPARγ occurs for several days, the drug can be removed and, while most cells remain viable, they retain a much reduced capacity for clonogenic growth. We [Hu, E. et al. *Science* 274:2100–2103 (1996)] and others [Adams et al., *J Biol Chem* 272:5128–5132 (1997); Camp et al., *J Biol Chem* 272:10811–10816 (1977)] have recently shown that PPARγ is a direct target for phosphorylation by MAP kinase and this modification results in a dramatic reduction in transcriptional and adipogenic activity of this receptor. Since many cancers, including breast cancer have been associated with elevated levels and/or activity of MAP kinase [Sivamaran, V. S. et al., *Journal Clinical Investigation* 99:1478–1483 (1997)], there is concern that this could be blocking PPARγ function in the process of malignancy and may also limit the effectiveness of activation of this receptor with synthetic compounds. Studies with the 21MT cell line show a synergistic effect of troglitazone with a MAP kinase inhibitor strongly suggest that this protein kinase can regulate PPARγ function in these cells.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for inhibiting proliferation of a PPARγ-responsive hyperproliferative cell, comprising contacting the cell with a) a PPARγ agonist in an amount effective to inhbit proliferation of the cell, and b) a MAP kinase inhibitor.

2. A method of treating or prophylactically preventing, in a subject animal, a disorder characterized by unwanted proliferation of PPARγ-responsive hyperproliferative cells, comprising administering to the animal a pharmaceutical preparation of a) a PPARγ agonist in an amount effective to inhibit growth of the PPARγ-responsive hyperproliferative cells, and b) a MAP kinase inhibitor.

3. The method of claim 1, wherein the PPARγ agonist is a ligand of a PPARγ protein, which ligand activates a transcriptional activity of the PPARγ protein.

4. The method of claim 1, wherein the PPARγ agonist is a thiazolidinedione, or an analog thereof.

5. The method of claim 1, wherein the PPARγ agonist is represented in the general formula:

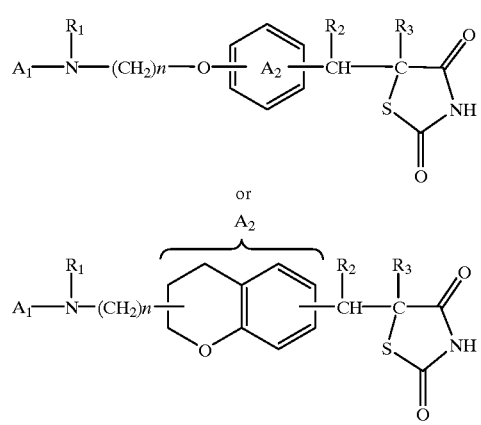

or a tautomeric form thereof, or a pharmaceutically acceptable salt thereof, or a pharmaceutically acceptable solvate thereof in which $A_1$ represents a substituted or unsubstituted aromatic heterocyclyl group; $R_1$ represents a hydrogen atom, an alkyl group, an acyl group, an aralkyl group, wherein the aryl moiety may be substituted or unsubstituted, or a substituted or unsubstituted aryl group; $R_2$ and $R_3$ each represent hydrogen, or $R_2$ and $R_3$ together represent a bond; $A_2$ represents a benzyl or chromanyl moiety having, as valence and stability permit, up to five substituents; and n represents an integer in the range of from 1 to 6.

6. The method of claim 5, wherein the PPARγ agonist is a compound selected from the group consisting of pioglitazone, troglitazone, ciglitazone, englitazone, and BRL49653.

7. The method of claim 1, wherein the PPARγ agonist is an arachidonate metabolite.

8. The method of claim 1, wherein the PPARγ agonist is a metabolite of $PGD_2$.

9. The method of claim 1, wherein the PPARγ agonist activates PPARγ-dependent transcription at a concentration at least one order of magnitude less than that required for the same level of activation of PPARα, PPARδ or RaR-dependent transcription.

10. The method of claim 1, further comprising contacting the cell with, or administering to the subject animal, an agent selected from the group consisting of mitotic inhibitors, alkylating agents, antimetabolites, nucleic acid intercalating agents, topoisomerase inhibitors, agents which promote apoptosis, and agents which increase immune responses to tumors.

11. The method of claim 1, wherein the MAP kinase inhibitor is PD098059.

12. The method of claim 1, wherein the cell is derived from an adipose cell or an adipose precursor cell.

13. The method of claim 12, wherein the cell is a liposarcoma cell.

14. The method of claim 1, wherein the cell is derived from an hemopoietic cell or an hemopoietic precursor cell.

15. The method of claim 14, wherein the cell is derived from malignant transformation of a cell of the lymphoid or myeloid lineage.

16. The method of claim 2, wherein the disorder comprises an adipose cell tumor.

17. The method of claim 16, wherein the adipose cell tumor disorder is selected from the group consisting of lipomas, fibrolipomas, lipoblastomas, lipomatosis, hibernomas, hemangiomas and liposarcomas.

18. The method of claim 16, wherein the adipose cell tumor disorder is a liposarcoma.

19. The method of claim 2, wherein the disorder is selected from the group consisting of sarcoma, carcinoma and leukemia.

20. The method of claim 19, wherein the disorder is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblascoma, craniopharyngioma, ependymoma, pinealoma, hemangioblastoma, acoustic neuroma, oligodendroglioma, meningioma, melanoma, neuroblastoma, and retinoblastoma.

21. The method of claim 19, wherein the disorder comprises a carcinoma forming from tissue of the breast, prostate, kidney, bladder or colon.

22. The method of claim 19, wherein the disorder comprises a leukemic cancer.

23. The method of claim 2, wherein the subject animal is a mammal.

24. The method of claim 23, wherein the subject animal is a human.

25. A pharmaceutical composition comprising: (i) a PRARγ agonist in a therpaeutically effective amount to induce terminal differentiation of a PPARγ-responsive hyperproliferative cell in a subject animal; (ii) at least one agent selected from the group consisting of mitotic inhibitors, alkylating agents, antimetabolites, nucleic acid intercalating agents, topoisomerase inhibitors, agents which promote apoptosis, and agents which increase immune responses to tumors; (iii) a MAP kinase inhibitor; and [(iii)] (iv) a pharmaceutically acceptable carrier.

26. A pharmaceutical composition comprising a PPARγ agonist and a MAP kinase inhibitor in a pharmaceutically acceptable carrier, the PPARγ agonist being present in a therpeutically effective amount to induce terminal differentiation of a PPARγ-responsive hyperproliferative cell in a subject animal.

27. The pharmaceutical composition of claim 25, wherein the PPARγ agonist is a thiazolidinedione, or an analog thereof.

28. The pharmaceutical composition of claim 25, wherein the PPARγ agonist is represented in the general formula:

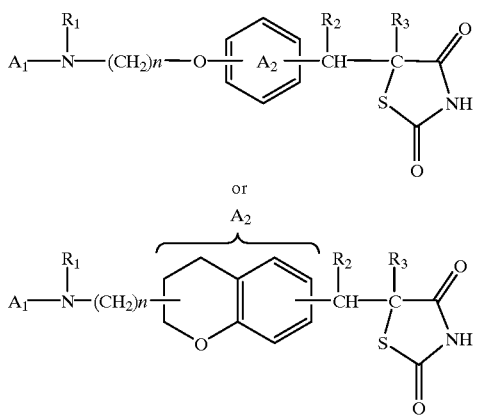

or a tautomeric form thereof, or a pharmaceutically acceptable salt thereof, or a pharmaceutically acceptable solvate thereof
in which $A_1$ represents a substituted or unsubstituted aromatic heterocyclyl group; $R_1$ represents a hydrogen atom, an alkyl group, an acyl group, an aralkyl group, wherein the aryl moiety may be substituted or unsubstituted, or a substituted or unsubstituted aryl group; $R_2$ and $R_3$ each represent hydrogen, or $R_2$ and $R_3$ together represent a bond; $A_2$ represents a benzyl or chromanyl moiety having, as valence and stability permit, up to five substituents; and n represents an integer in the range of from 1 to 6.

29. The pharmaceutical composition of claim 28, wherein the PPARγ agonist is a compound selected from the group of pioglitazone, troglitazone, ciglitazone, englitazone, and BRL49653.

30. The pharmaceutical composition of claim 25, wherein the PPARγ agonist is an arachidonate metabolite.

31. The pharmaceutical composition of claim 30, wherein the PPARγ agonist is a metabolite of $PGD_2$.

32. The pharmaceutical composition of claim 25, wherein the PPARγ agonist activates PPARγ-dependent transcription at a concentration at least one order of magnitude less than required for the same level of activation of PPARα, PPARδ or RaR-dependent transcription.

33. The pharmaceutical composition of claim 26, wherein the MAP kinase inhibitor is PD098059.

34. The method of claim 1, wherein inhibiting proliferation of the cell induces differentiation of the cell to a phenotype of lower proliferative index.

35. The method of claim 2, wherein the MAP kinase inhibitor is PD098059.

* * * * *